US012703755B2

(12) United States Patent
Shi et al.

(10) Patent No.: US 12,703,755 B2
(45) Date of Patent: Aug. 11, 2026

(54) ANTIBODY TARGETING BCMA, BISPECIFIC ANTIBODY, AND USE THEREOF

(71) Applicant: Harbour Biomed (Shanghai) Co., Ltd, Shanghai (CN)

(72) Inventors: Lei Shi, Suzhou (CN); Xuekun Zhang, Suzhou (CN); Yun He, Suzhou (CN); Jianxun Zhao, Suzhou (CN); Wei Zhou, Suzhou (CN); Fei Chen, Suzhou (CN); Xiangyang Tan, Suzhou (CN); Yiping Rong, Suzhou (CN)

(73) Assignee: HARBOUR BIOMED (SUZHOU) CO., LTD., Suzhou (CN)

( * ) Notice: Subject to any disclaimer, the term of this patent is extended or adjusted under 35 U.S.C. 154(b) by 1041 days.

(21) Appl. No.: 17/764,308

(22) PCT Filed: Sep. 29, 2020

(86) PCT No.: PCT/CN2020/118780
§ 371 (c)(1),
(2) Date: Mar. 28, 2022

(87) PCT Pub. No.: WO2021/063349
PCT Pub. Date: Apr. 8, 2021

(65) Prior Publication Data

US 2022/0340673 A1 Oct. 27, 2022

(30) Foreign Application Priority Data

Sep. 30, 2019 (CN) ......................... 201910941311.0

(51) Int. Cl.

| | |
|---|---|
| ***C07K 16/28*** | (2006.01) |
| ***A61K 47/68*** | (2017.01) |
| ***A61P 35/00*** | (2006.01) |
| *A61K 39/00* | (2006.01) |

(52) U.S. Cl.
CPC ...... *C07K 16/2878* (2013.01); *A61K 47/6849* (2017.08); *A61P 35/00* (2018.01); *C07K 16/2809* (2013.01); *A61K 2039/505* (2013.01); *C07K 2317/21* (2013.01); *C07K 2317/24* (2013.01); *C07K 2317/31* (2013.01); *C07K 2317/53* (2013.01); *C07K 2317/565* (2013.01); *C07K 2317/732* (2013.01); *C07K 2317/734* (2013.01); *C07K 2317/76* (2013.01); *C07K 2317/92* (2013.01)

(58) Field of Classification Search
CPC ............ C07K 16/2878; C07K 16/2809; C07K 2317/21; C07K 2317/24; C07K 2317/31; C07K 2317/53; C07K 2317/565; C07K 2317/732; C07K 2317/734; C07K 2317/76; C07K 2317/92; C07K 2317/33; C07K 2317/524; C07K 2317/569; C07K 2317/73; C07K 2317/52; C07K 2317/94; A61K 47/6849; A61K 2039/505; A61K 2039/545; A61K 47/6851; A61K 39/395; A61K 47/6803; A61P 35/00; C12N 15/85
See application file for complete search history.

(56) References Cited

U.S. PATENT DOCUMENTS

| | | | | |
|---|---|---|---|---|
| 8,846,042 | B2 | 9/2014 | Zhou | |
| 9,556,264 | B2 | 1/2017 | Shiraiwa et al. | |
| 10,562,972 | B2 | 2/2020 | Brentjens et al. | |
| 10,815,304 | B2 | 10/2020 | Qu et al. | |
| 2007/0148164 | A1* | 6/2007 | Farrington | A61P 35/00 435/328 |
| 2020/0048348 | A1 | 2/2020 | Trinklein et al. | |

FOREIGN PATENT DOCUMENTS

| | | | | |
|---|---|---|---|---|
| CN | 103842383 | A | 6/2014 | |
| CN | 107206076 | A | 9/2017 | |
| CN | 104136610 | B | 5/2018 | |
| CN | 109485734 | A | 3/2019 | |
| CN | 109694413 | A | 4/2019 | |
| CN | 109843325 | A | 6/2019 | |
| CN | 109942708 | A * | 6/2019 | |
| WO | WO-2002085945 | A3 | 3/2003 | |
| WO | WO-2009073533 | A2 * | 6/2009 | A61K 47/48438 |
| WO | WO-2009080251 | A1 | 7/2009 | |

(Continued)

OTHER PUBLICATIONS

Rudikoff et al. Proceedings of the National Academy of Sciences USA, vol. 79, p. 1979-1983, 1982 (Year: 1982).*

(Continued)

*Primary Examiner* — Sean E Aeder
*Assistant Examiner* — Yie Chia Lee
(74) *Attorney, Agent, or Firm* — Harness, Dickey & Pierce, P.L.C.

(57) ABSTRACT

Provided are an antibody targeting BCMA, a bispecific antibody targeting BCMA and CD3, and applications thereof. The antibody targeting BCMA comprises two heavy chain variable regions, the heavy chain variable regions comprising HCDR1, HCDR2, and HCDR3 as shown in the amino acid sequences of SEQ ID NO: 22, SEQ ID NO: 33 and SEQ ID NO: 42, or HCDR1, HCDR2, and HCDR3 as shown in the amino acid sequences of SEQ ID NO: 26, SEQ ID NO: 37 and SEQ ID NO: 41. The antibody effectively targets human BCMA and binds to cynomolgus BCMA; the bispecific antibody effectively targets both human BCMA and human CD3, and can bind to cynomolgus BCMA and cynomolgus CD3.

13 Claims, 18 Drawing Sheets

Specification includes a Sequence Listing.

(56) References Cited

FOREIGN PATENT DOCUMENTS

| | | | |
|---|---|---|---|
| WO | WO-2009080252 | A1 | 7/2009 |
| WO | WO-2017084495 | A1 | 5/2017 |
| WO | 2017125897 | A1 | 7/2017 |
| WO | WO-2018052503 | A1 | 3/2018 |
| WO | WO-2018119215 | A1 | 6/2018 |
| WO | 2018140845 | A2 | 8/2018 |

OTHER PUBLICATIONS

Kappell et al., Current Opinions in Biotechnology, vol. 3, p. 548-553, 1992 (Year: 1992).*
Paul, Fundamental Immunology, 3rd Edition, 1993, pp. 292-295 (Year: 1993).*
Houdebine et al., Journal of Biotechnology, vol. 34, p. 269-287, 1994 (Year: 1994).*
Bendig M. M. Methods: A Companion to Methods in Enzymology, 1995; 8:83-93 (Year: 1995).*
Wall et al., Theriogenology, vol. 45, p. 57-68, 1996 (Year: 1996).*
Evans et al. Q. J. Med 1999: 92: 299-307 (Year: 1999).*
Cuzick et al. The Lancet, vol. 361, p. 296-300, 2003 (Year: 2003).*
Komenaka et al., Clinics in Dermatology, 2004, vol. 22, p. 251-265 (Year: 2004).*
Schiffman et al., The New England Journal of Medicine, Vo. 353, No. 20, p. 2101-2104, 2005 (Year: 2005).*
Houdebine. Comparative Immunology, Microbiology, and Infectious Diseases, vol. 32, p. 107-121, 2009 (Year: 2009).*
Hernandez-Ledesma Peptides, vol. 30, p. 426-430, 2009 (Year: 2009).*
Cohen et al. First in human study with GSK2857916, an antibody drug conjugated to microtubule-disrupting agent directed against B-cell maturation antigen (BCMA) in patients with relapsed/refractory multiple myeloma (MM): results from study BMA117159 part 1 dose escalation. Blood 128.22 (2016): 1148. (Year: 2016).*
Sedykh et al. "Bispecific antibodies: design, therapy, perspectives." Drug design, development and therapy (2018): 195-208. (Year: 2018).*
Jan. 7, 2021 International Search Report issued in International Patent Application No. PCT/CN2020/118780.
Jan. 7, 2021 Written Opinion of the International Searching Authority issued in International Patent Application No. PCT/CN2020/118780.
Nov. 25, 2021 Taiwan Office Action issued in Patent Application No. 109133807.
Seckinger,A, et al. "Target Expression, Generation, Preclinical Activity, and Pharmacokinetics of the BCMA-T Cell Bispecific Antibody EM801 for Multiple Myeloma Treatment", Cancer Cell, vol. 31, Mar. 13, 2017 (Mar. 13, 2017), pp. 396-410.
Ahamadi-Fesharaki, R. et al. "Single-Chain Variable Fragment-Based Bispecific Antibodies: Hitting Two Targets with One Sophisticated Arrow", Molecular Therapy: Oncolytics, vol. 14, Mar. 23, 2019 (Mar. 23, 2019), pp. 38-56.
Trinklein ND, Pham D, Schellenberger U, et al. Efficient tumor killing and minimal cytokine release with novel T-cell agonist bispecific antibodies. MAbs. 2019;11(4):639-652.
Buelow B, Pham D, Clarke S, et al. Development of a fully human T cell engaging bispecific antibody for the treatment of multiple myeloma[J]. 2017.
Jun. 2, 2023 Search Report issued in Chinese Patent Application No. 202080068742.1.
Jun. 2, 2023 First Office Action issued in Chinese Patent Application No. 202080068742.1.
Hipp et al. Leukemia 31, 1743-1751; 2017 (Year: 2017).
Byers, T. CA Cancer Journal for Clinicians, vol. 49, No. 6, Nov./Dec. 1999 (Year: 1999).

* cited by examiner

| | Antibody | maximum fluorescence values | EC50 (nM) |
|---|---|---|---|
| HEK293T cell strain overexpressing human BCMA | PR001046 | 63382 | 0.213 |
| | Positive control 1 | 86498 | 4.067 |
| HEK293T cell strain overexpressing cynomolgus monkey BCMA | PR001046 | 67701 | 0.564 |
| | Positive control 1 | 158037 | 4.564 |
| NCI-H929 cell line | PR001046 | 132791 | 1.535 |
| | Positive control 1 | 124959 | 10.75 |

| Antibody | IC50(nM) |
|---|---|
| PR001046 | 2.94 |
| Positive control 1 | 4.36 |

| Antibody | maximum fluorescence values | EC50 (nM) |
| --- | --- | --- |
| PR003178 | 5213 | 1.1 |
| Positive control 2 | 6098 | 8.7 |
| PR002299 | 3552 | 57.2 |

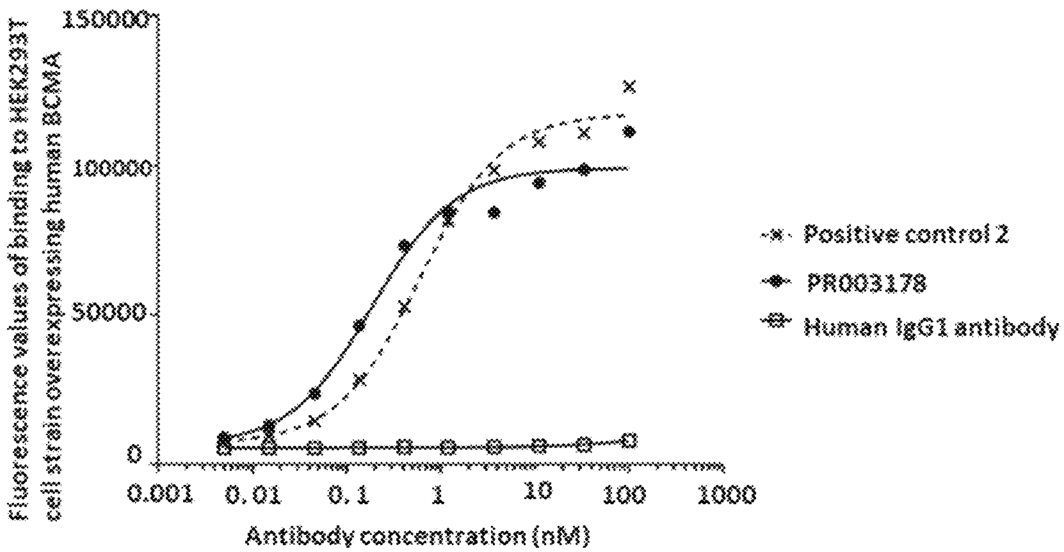
Fig. 4A
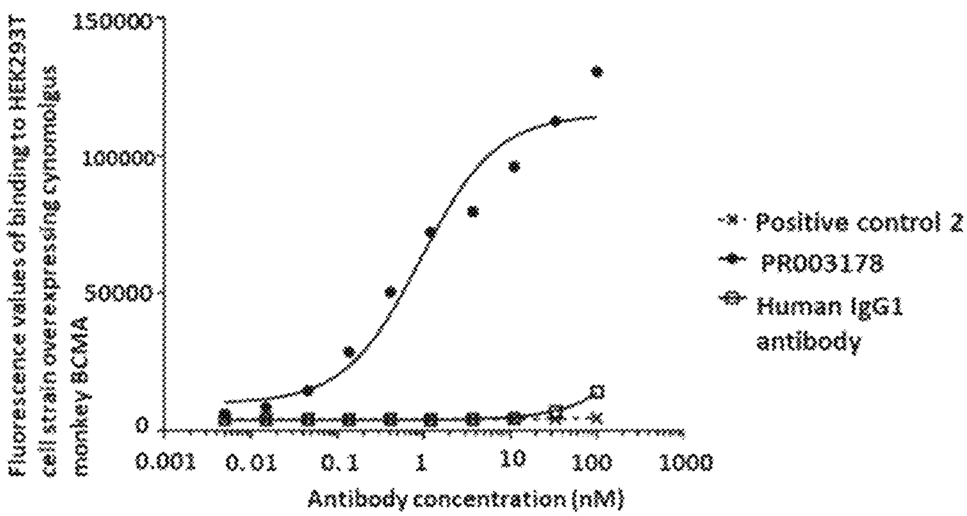
Fig. 4B
| | Antibody | maximum fluorescence values | EC50 (nM) |
|---|---|---|---|
| HEK293T cell strain overexpressing human BCMA | PR003187 | 99267 | 0.188 |
| | Positive control 2 | 117412 | 0.602 |
| HEK293T cell strain overexpressing cynomolgus monkey BCMA | PR003187 | 115022 | 0.921 |
| | Positive control 2 | 4698 | N/A |
Fig. 4C

| | Antibody | Max killing % | EC50 (nM) |
|---|---|---|---|
| Killing of NCI-H929 | PR003178 | 51.9 | 0.041 |
| | Positive control 2 | 41.02 | 0.467 |

| | Antibody | Max values (pg/mL) | EC50 (nM) |
|---|---|---|---|
| Release of IL-6 | PR003178 | 27.33 | 0.154 |
| | Positive control 2 | 10.31 | 0.709 |
| Release of TNF-α | PR003178 | 1148 | 0.096 |
| | Positive control 2 | 594 | 1.319 |

| | Antibody | Max killing % | EC50 (nM) |
|---|---|---|---|
| Killing of RPMI-8226 | PR003178 | 27.81 | 0.144 |
| | Positive control 2 | 19.16 | 0.195 |

Fig. 7D

| | Antibody | Max values (pg/mL) | EC50 (nM) |
|---|---|---|---|
| Release of IL-6 | PR003178 | 118.2 | 0.011 |
| | Positive control 2 | 87.2 | 0.131 |
| Release of TNF-α | PR003178 | 75.5 | 0.083 |
| | Positive control 2 | 44.7 | 4.4 |

Fig. 7E

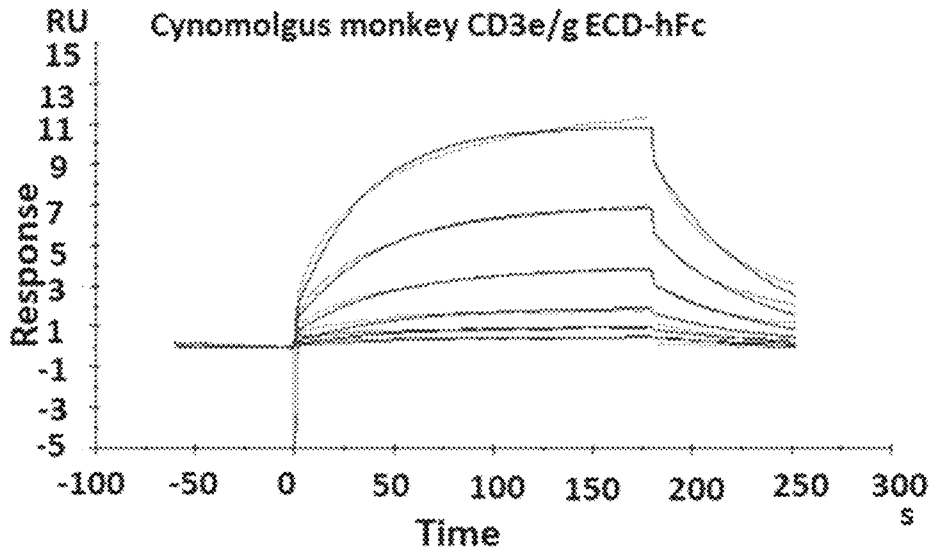
Fig. 11C
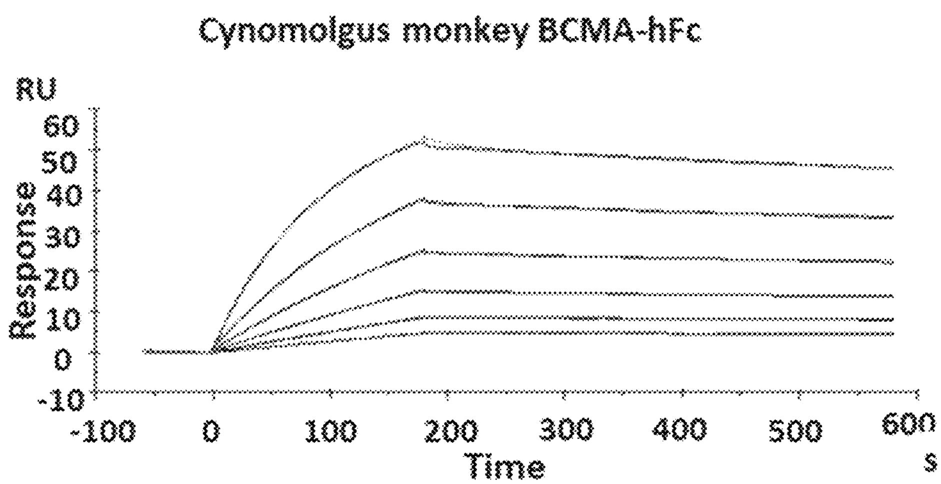
Fig. 11D
| Ab name | Ag name | Conc. Of Ab(nM) | ka(1/Ms) | kd(1/s) | KD (M) | Test Date |
|---|---|---|---|---|---|---|
| PR003178 | hBCMA | 12-0.375 | 1.761E+06 | 1.671E-04 | 9.493E-11 | 2019.9.3 |
| | cyno BCMA | 6-0.1875 | 1.938E+06 | 2.854E-04 | 1.473E-10 | 2019.9.4 |
| | hCD3 | 12-0.375 | 5.875E+05 | 1.493E-02 | 2.541E-08 | 2019.9.3 |
| | cyno CD3 | 25-0.781 | 4.289E+05 | 1.790E-02 | 4.173E-08 | 2019.9.2 |
Fig. 11E

SEQUENCE LISTING

```
<160> NUMBER OF SEQ ID NOS: 69

<210> SEQ ID NO 1
<211> LENGTH: 354
<212> TYPE: PRT
<213> ORGANISM: Artificial Sequence
<220> FEATURE:
<223> OTHER INFORMATION: HC of antibody PR001046, Chothia definition

<400> SEQUENCE: 1

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Val Ser Asp Asn
            20                  25                  30

Tyr Met Thr Trp Val Arg Gln Ala Pro Gly Lys Gly Leu Glu Trp Val
        35                  40                  45

Ser Val Ile Phe Ser Gly Gly Asn Thr Tyr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Leu Tyr Tyr Cys Ala
                85                  90                  95

Arg Arg Asn Tyr Asp Asp Thr Arg Gly Thr Asp Val Phe Asp Ile Trp
            100                 105                 110

Gly Gln Gly Thr Met Val Thr Val Ser Ser Glu Pro Lys Ser Cys Asp
        115                 120                 125

Lys Thr His Thr Cys Pro Pro Cys Pro Ala Pro Glu Leu Leu Gly Gly
    130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190
```

-continued

```
Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
    210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Arg Glu Glu Met Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
    290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
            340                 345                 350

Gly Lys


<210> SEQ ID NO 2
<211> LENGTH: 451
<212> TYPE: PRT
<213> ORGANISM: Artificial Sequence
<220> FEATURE:
<223> OTHER INFORMATION: HC of antibody PR000274 , Chothia definition

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Tyr Asp Gly Tyr Asp Val Leu Asp Asn Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 3
<211> LENGTH: 453
<212> TYPE: PRT
<213> ORGANISM: Artificial Sequence
<220> FEATURE:
<223> OTHER INFORMATION: HC1 of antibody PR002199, Chothia definition

<400> SEQUENCE: 3

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95
```

-continued

```
Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Gly Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Glu Glu Met Thr Lys Asn Gln
        355                 360                 365

Val Ser Leu Trp Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 4
<211> LENGTH: 455
<212> TYPE: PRT
<213> ORGANISM: Artificial Sequence
<220> FEATURE:
<223> OTHER INFORMATION: HC1 of antibody PR002299, Chothia definition

<400> SEQUENCE: 4

-continued

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Gly Ala Pro Ile Glu Lys Thr Ile Ser Lys Ala Lys Gly Gln Pro Arg
            340                 345                 350

Glu Pro Gln Val Tyr Thr Leu Pro Pro Cys Arg Glu Glu Met Thr Lys
        355                 360                 365

Asn Gln Val Ser Leu Trp Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
```

```
            420                 425                 430

Cys Ser Val Met His Glu Ala Leu His Asn His Tyr Thr Gln Lys Ser
        435                 440                 445

Leu Ser Leu Ser Pro Gly Lys
    450                 455


<210> SEQ ID NO 5
<211> LENGTH: 455
<212> TYPE: PRT
<213> ORGANISM: Artificial Sequence
<220> FEATURE:
<223> OTHER INFORMATION: HC1 of antibody PR003178, Chothia definition

<400> SEQUENCE: 5

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
```

```
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Cys Arg Glu Glu Met Thr Lys
        355                 360                 365

Asn Gln Val Ser Leu Trp Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455


<210> SEQ ID NO 6
<211> LENGTH: 477
<212> TYPE: PRT
<213> ORGANISM: Artificial Sequence
<220> FEATURE:
<223> OTHER INFORMATION: HC2 of antibody PR002199, Chothia definition

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Ala Pro Gly Lys Gly Pro Glu Trp Val
        35                  40                  45

Ser Gly Ile Arg Gly Ser Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Glu Asn Asp Gly Pro Phe Asp His Arg Gly Gln Gly
            100                 105                 110

Thr Leu Val Thr Val Ser Ser Gly Gly Gly Gly Ser Glu Val Gln Leu
        115                 120                 125

Leu Glu Ser Gly Gly Gly Leu Val Gln Pro Gly Gly Ser Leu Arg Leu
    130                 135                 140

Ser Cys Ala Ala Ser Gly Phe Thr Val Ser Ser Tyr Gly Met Ser Trp
145                 150                 155                 160

Val Arg Gln Ala Pro Gly Lys Gly Pro Glu Trp Val Ser Gly Ile Arg
                165                 170                 175

Gly Ser Asp Gly Ser Thr Tyr Tyr Ala Asp Ser Val Lys Gly Arg Phe
            180                 185                 190

Thr Ile Ser Arg Asp Asn Ser Lys Asn Thr Leu Tyr Leu Gln Met Asn
        195                 200                 205

Ser Leu Arg Ala Glu Asp Thr Ala Val Tyr Tyr Cys Ala Lys Gln Gly
    210                 215                 220

Glu Asn Asp Gly Pro Phe Asp His Arg Gly Gln Gly Thr Leu Val Thr
```

```
225                 230                 235                 240

Val Ser Ser Ala Ser Glu Pro Lys Ser Ser Asp Lys Thr His Thr Cys
            245                 250                 255

Pro Pro Cys Pro Ala Pro Glu Ala Ala Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
            325                 330                 335

Thr Val Leu His Gln Asp Trp Leu Asn Gly Lys Glu Tyr Lys Cys Lys
            340                 345                 350

Val Ser Asn Lys Ala Leu Gly Ala Pro Ile Glu Lys Thr Ile Ser Lys
        355                 360                 365

Ala Lys Gly Gln Pro Arg Glu Pro Gln Val Cys Thr Leu Pro Pro Ser
    370                 375                 380

Arg Glu Glu Met Thr Lys Asn Gln Val Ser Leu Ser Cys Ala Val Lys
385                 390                 395                 400

Gly Phe Tyr Pro Ser Asp Ile Ala Val Glu Trp Glu Ser Asn Gly Gln
            405                 410                 415

Pro Glu Asn Asn Tyr Lys Thr Thr Pro Pro Val Leu Asp Ser Asp Gly
            420                 425                 430

Ser Phe Phe Leu Val Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys
465                 470                 475


<210> SEQ ID NO 7
<211> LENGTH: 487
<212> TYPE: PRT
<213> ORGANISM: Artificial Sequence
<220> FEATURE:
<223> OTHER INFORMATION: HC2 of antibody PR002299, Chothia definition

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ile Trp Val Arg Gln Ala Pro Gly Lys Gly Leu Glu Trp Val
        35                  40                  45

Ser Gly Ile Ser Glu Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
            85                  90                  95

Val Lys Asp Leu Asp Asp Ile Leu Thr Gly Tyr Tyr Lys Asp Tyr Trp
            100                 105                 110

Gly Gln Gly Thr Leu Val Thr Val Ser Ser Arg Thr Gly Gly Gly Gly
```

-continued

```
        115                 120                 125

Ser Lys Leu Glu Val Gln Leu Leu Glu Ser Gly Gly Gly Leu Val Gln
    130                 135                 140

Pro Gly Gly Ser Leu Arg Leu Ser Cys Ala Ala Ser Gly Phe Thr Phe
145                 150                 155                 160

Ser Ser Tyr Ala Met Ile Trp Val Arg Gln Ala Pro Gly Lys Gly Leu
                165                 170                 175

Glu Trp Val Ser Gly Ile Ser Glu Ser Gly Gly Ser Thr Tyr Tyr Ala
            180                 185                 190

Asp Ser Val Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
    210                 215                 220

Tyr Phe Cys Val Lys Asp Leu Asp Asp Ile Leu Thr Gly Tyr Tyr Lys
225                 230                 235                 240

Asp Tyr Trp Gly Gln Gly Thr Leu Val Thr Val Ser Ser Ala Ser Glu
                245                 250                 255

Pro Lys Ser Ser Asp Lys Thr His Thr Cys Pro Pro Cys Pro Ala Pro
            260                 265                 270

Glu Ala Ala Gly Gly Pro Ser Val Phe Leu Phe Pro Pro Lys Pro Lys
        275                 280                 285

Asp Thr Leu Met Ile Ser Arg Thr Pro Glu Val Thr Cys Val Val Val
    290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                325                 330                 335

Asn Ser Thr Tyr Arg Val Val Ser Val Leu Thr Val Leu His Gln Asp
            340                 345                 350

Trp Leu Asn Gly Lys Glu Tyr Lys Cys Lys Val Ser Asn Lys Ala Leu
        355                 360                 365

Gly Ala Pro Ile Glu Lys Thr Ile Ser Lys Ala Lys Gly Gln Pro Arg
    370                 375                 380

Glu Pro Gln Val Cys Thr Leu Pro Pro Ser Arg Glu Glu Met Thr Lys
385                 390                 395                 400

Asn Gln Val Ser Leu Ser Cys Ala Val Lys Gly Phe Tyr Pro Ser Asp
                405                 410                 415

Ile Ala Val Glu Trp Glu Ser Asn Gly Gln Pro Glu Asn Asn Tyr Lys
            420                 425                 430

Thr Thr Pro Pro Val Leu Asp Ser Asp Gly Ser Phe Phe Leu Val Ser
        435                 440                 445

Lys Leu Thr Val Asp Lys Ser Arg Trp Gln Gln Gly Asn Val Phe Ser
    450                 455                 460

Cys Ser Val Met His Glu Ala Leu His Asn His Tyr Thr Gln Lys Ser
465                 470                 475                 480

Leu Ser Leu Ser Pro Gly Lys
                485
```

<210> SEQ ID NO 8
<211> LENGTH: 493
<212> TYPE: PRT
<213> ORGANISM: Artificial Sequence
<220> FEATURE:
<223> OTHER INFORMATION: HC2 of antibody PR003178, Chothia definition

<400> SEQUENCE: 8

```
Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Val Ser Asp Asn
            20                  25                  30

Tyr Met Thr Trp Val Arg Gln Ala Pro Gly Lys Gly Leu Glu Trp Val
        35                  40                  45

Ser Val Ile Phe Ser Gly Gly Asn Thr Tyr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Leu Tyr Tyr Cys Ala
                85                  90                  95

Arg Arg Asn Tyr Asp Asp Thr Arg Gly Thr Asp Val Phe Asp Ile Trp
            100                 105                 110

Gly Gln Gly Thr Met Val Thr Val Ser Ser Gly Gly Gly Gly Ser Gly
        115                 120                 125

Gly Gly Gly Ser Gly Gly Gly Gly Ser Glu Val Gln Leu Val Glu Thr
    130                 135                 140

Gly Gly Gly Leu Ile Gln Pro Gly Gly Ser Leu Arg Leu Ser Cys Ala
145                 150                 155                 160

Ala Ser Gly Phe Thr Val Ser Asp Asn Tyr Met Thr Trp Val Arg Gln
                165                 170                 175

Ala Pro Gly Lys Gly Leu Glu Trp Val Ser Val Ile Phe Ser Gly Gly
            180                 185                 190

Asn Thr Tyr Tyr Ala Asp Ser Val Lys Gly Arg Phe Thr Ile Ser Arg
        195                 200                 205

Asp Asn Ala Lys Asn Thr Leu Tyr Leu Gln Met Asn Ser Leu Arg Ala
    210                 215                 220

Glu Asp Thr Ala Leu Tyr Tyr Cys Ala Arg Arg Asn Tyr Asp Asp Thr
225                 230                 235                 240

Arg Gly Thr Asp Val Phe Asp Ile Trp Gly Gln Gly Thr Met Val Thr
                245                 250                 255

Val Ser Ser Ala Ser Glu Pro Lys Ser Ser Asp Lys Thr His Thr Cys
            260                 265                 270

Pro Pro Cys Pro Ala Pro Glu Ala Ala Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Cys Thr Leu Pro Pro Ser
385                 390                 395                 400

Arg Glu Glu Met Thr Lys Asn Gln Val Ser Leu Ser Cys Ala Val Lys
                405                 410                 415
```

```
Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Val Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490


<210> SEQ ID NO 9
<211> LENGTH: 5
<212> TYPE: PRT
<213> ORGANISM: Artificial Sequence
<220> FEATURE:
<223> OTHER INFORMATION: HCDR1 of antibody PR000274, Kabat definition

<400> SEQUENCE: 9

Asn Tyr Trp Met His
1               5


<210> SEQ ID NO 10
<211> LENGTH: 5
<212> TYPE: PRT
<213> ORGANISM: Artificial Sequence
<220> FEATURE:
<223> OTHER INFORMATION: HCDR1 of antibody PR001046 or VH2 HCDR1 of
      antibody PR003178, Kabat definition

<400> SEQUENCE: 10

Asp Asn Tyr Met Thr
1               5


<210> SEQ ID NO 11
<211> LENGTH: 5
<212> TYPE: PRT
<213> ORGANISM: Artificial Sequence
<220> FEATURE:
<223> OTHER INFORMATION: VH1 HCDR1 of antibody PR002199, Kabat
      definition

<400> SEQUENCE: 11

Asp Tyr Ala Met His
1               5


<210> SEQ ID NO 12
<211> LENGTH: 5
<212> TYPE: PRT
<213> ORGANISM: Artificial Sequence
<220> FEATURE:
<223> OTHER INFORMATION: VH2 HCDR1 of antibody PR002199, Kabat
      definition

<400> SEQUENCE: 12

Ser Tyr Gly Met Ser
1               5


<210> SEQ ID NO 13
<211> LENGTH: 5
<212> TYPE: PRT
<213> ORGANISM: Artificial Sequence
<220> FEATURE:
<223> OTHER INFORMATION: VH1 HCDR1 of antibody PR002299 or PR003178,
      Kabat definition
```

<400> SEQUENCE: 13

Thr Tyr Ala Met Asn
1 5

<210> SEQ ID NO 14
<211> LENGTH: 5
<212> TYPE: PRT
<213> ORGANISM: Artificial Sequence
<220> FEATURE:
<223> OTHER INFORMATION: VH2 HCDR1 of antibody PR002299, Kabat definition

<400> SEQUENCE: 14

Ser Tyr Ala Met Ile
1 5

<210> SEQ ID NO 15
<211> LENGTH: 7
<212> TYPE: PRT
<213> ORGANISM: Artificial Sequence
<220> FEATURE:
<223> OTHER INFORMATION: HCDR1 of antibody PR000274, Chothia definition

<400> SEQUENCE: 15

Gly Gly Thr Phe Ser Asn Tyr
1 5

<210> SEQ ID NO 16
<211> LENGTH: 7
<212> TYPE: PRT
<213> ORGANISM: Artificial Sequence
<220> FEATURE:
<223> OTHER INFORMATION: HCDR1 of antibody PR001046 or VH2 HCDR1 of PR003178, Chothia definition

<400> SEQUENCE: 16

Gly Phe Thr Val Ser Asp Asn
1 5

<210> SEQ ID NO 17
<211> LENGTH: 7
<212> TYPE: PRT
<213> ORGANISM: Artificial Sequence
<220> FEATURE:
<223> OTHER INFORMATION: VH1 HCDR1 of antibody PR002199, Chothia definition

<400> SEQUENCE: 17

Gly Phe Thr Phe Asp Asp Tyr
1 5

<210> SEQ ID NO 18
<211> LENGTH: 7
<212> TYPE: PRT
<213> ORGANISM: Artificial Sequence
<220> FEATURE:
<223> OTHER INFORMATION: VH2 HCDR1 of antibody PR002199, Chothia definition

<400> SEQUENCE: 18

Gly Phe Thr Val Ser Ser Tyr
1 5

<210> SEQ ID NO 19
<211> LENGTH: 7
<212> TYPE: PRT

-continued

<213> ORGANISM: Artificial Sequence
<220> FEATURE:
<223> OTHER INFORMATION: VH1 HCDR1 of antibody PR002299 or antibody PR003178, Chothia definition

<400> SEQUENCE: 19

Gly Phe Thr Phe Ser Thr Tyr
1               5

<210> SEQ ID NO 20
<211> LENGTH: 7
<212> TYPE: PRT
<213> ORGANISM: Artificial Sequence
<220> FEATURE:
<223> OTHER INFORMATION: VH2 HCDR1 of antibody PR002299, Chothia definition

<400> SEQUENCE: 20

Gly Phe Thr Phe Ser Ser Tyr
1               5

<210> SEQ ID NO 21
<211> LENGTH: 10
<212> TYPE: PRT
<213> ORGANISM: Artificial Sequence
<220> FEATURE:
<223> OTHER INFORMATION: HCDR1 of antibody PR000274, Combined definition

<400> SEQUENCE: 21

Gly Gly Thr Phe Ser Asn Tyr Trp Met His
1               5                   10

<210> SEQ ID NO 22
<211> LENGTH: 10
<212> TYPE: PRT
<213> ORGANISM: Artificial Sequence
<220> FEATURE:
<223> OTHER INFORMATION: HCDR1 of antibody PR001046 or VH2 HCDR1 of antibody PR003178, Combined definition

<400> SEQUENCE: 22

Gly Phe Thr Val Ser Asp Asn Tyr Met Thr
1               5                   10

<210> SEQ ID NO 23
<211> LENGTH: 10
<212> TYPE: PRT
<213> ORGANISM: Artificial Sequence
<220> FEATURE:
<223> OTHER INFORMATION: VH1 HCDR1 of antibody PR002199, Combined definition

<400> SEQUENCE: 23

Gly Phe Thr Phe Asp Asp Tyr Ala Met His
1               5                   10

<210> SEQ ID NO 24
<211> LENGTH: 10
<212> TYPE: PRT
<213> ORGANISM: Artificial Sequence
<220> FEATURE:
<223> OTHER INFORMATION: VH2 HCDR1 of antibody PR002199, Combined definition

<400> SEQUENCE: 24

Gly Phe Thr Val Ser Ser Tyr Gly Met Ser
1               5                   10

<210> SEQ ID NO 25
<211> LENGTH: 10
<212> TYPE: PRT
<213> ORGANISM: Artificial Sequence
<220> FEATURE:
<223> OTHER INFORMATION: VH1 HCDR1 of antibody PR002299 or PR003178, Combined definition

<400> SEQUENCE: 25

Gly Phe Thr Phe Ser Thr Tyr Ala Met Asn
1               5                   10

<210> SEQ ID NO 26
<211> LENGTH: 10
<212> TYPE: PRT
<213> ORGANISM: Artificial Sequence
<220> FEATURE:
<223> OTHER INFORMATION: VH2 HCDR1 of antibody PR002299, Combined definition

<400> SEQUENCE: 26

Gly Phe Thr Phe Ser Ser Tyr Ala Met Ile
1               5                   10

<210> SEQ ID NO 27
<211> LENGTH: 5
<212> TYPE: PRT
<213> ORGANISM: Artificial Sequence
<220> FEATURE:
<223> OTHER INFORMATION: HCDR2 of antibody PR001046 or VH2 HCDR2 of PR003178, Chothia definition

<400> SEQUENCE: 27

Phe Ser Gly Gly Asn
1               5

<210> SEQ ID NO 28
<211> LENGTH: 6
<212> TYPE: PRT
<213> ORGANISM: Artificial Sequence
<220> FEATURE:
<223> OTHER INFORMATION: HCDR2 of antibody PR000274, Chothia definition

<400> SEQUENCE: 28

Tyr Arg Gly His Ser Asp
1               5

<210> SEQ ID NO 29
<211> LENGTH: 6
<212> TYPE: PRT
<213> ORGANISM: Artificial Sequence
<220> FEATURE:
<223> OTHER INFORMATION: VH1 HCDR2 of antibody PR002199, Chothia definition

<400> SEQUENCE: 29

Ser Trp Asn Ser Gly Ser
1               5

<210> SEQ ID NO 30
<211> LENGTH: 6
<212> TYPE: PRT
<213> ORGANISM: Artificial Sequence
<220> FEATURE:
<223> OTHER INFORMATION: VH2 HCDR2 of antibody PR002199, Chothia definition

<400> SEQUENCE: 30

-continued

Arg Gly Ser Asp Gly Ser
1 5

<210> SEQ ID NO 31
<211> LENGTH: 6
<212> TYPE: PRT
<213> ORGANISM: Artificial Sequence
<220> FEATURE:
<223> OTHER INFORMATION: VH2 HCDR2 of antibody PR002299, Chothia definition

<400> SEQUENCE: 31

Ser Glu Ser Gly Gly Ser
1 5

<210> SEQ ID NO 32
<211> LENGTH: 8
<212> TYPE: PRT
<213> ORGANISM: Artificial Sequence
<220> FEATURE:
<223> OTHER INFORMATION: VH1 HCDR2 of antibody PR002299 or PR003178, Chothia definition

<400> SEQUENCE: 32

Arg Ser Lys Tyr Asn Asn Tyr Ala
1 5

<210> SEQ ID NO 33
<211> LENGTH: 16
<212> TYPE: PRT
<213> ORGANISM: Artificial Sequence
<220> FEATURE:
<223> OTHER INFORMATION: HCDR2 of antibody PR001046 or VH2 HCDR2 of antibody PR003178, Combined or Kabat definition

<400> SEQUENCE: 33

Val Ile Phe Ser Gly Gly Asn Thr Tyr Tyr Ala Asp Ser Val Lys Gly
1 5 10 15

<210> SEQ ID NO 34
<211> LENGTH: 17
<212> TYPE: PRT
<213> ORGANISM: Artificial Sequence
<220> FEATURE:
<223> OTHER INFORMATION: HCDR2 of antibody PR000274, Combined or Kabat definition

<400> SEQUENCE: 34

Ala Thr Tyr Arg Gly His Ser Asp Thr Tyr Tyr Asn Gln Lys Phe Lys
1 5 10 15

Gly

<210> SEQ ID NO 35
<211> LENGTH: 17
<212> TYPE: PRT
<213> ORGANISM: Artificial Sequence
<220> FEATURE:
<223> OTHER INFORMATION: VH1 HCDR2 of antibody PR002199, Combined or Kabat definition

<400> SEQUENCE: 35

Gly Ile Ser Trp Asn Ser Gly Ser Ile Gly Tyr Ala Asp Ser Val Lys
1 5 10 15

Gly

<210> SEQ ID NO 36
<211> LENGTH: 17
<212> TYPE: PRT
<213> ORGANISM: Artificial Sequence
<220> FEATURE:
<223> OTHER INFORMATION: VH2 HCDR2 of antibody PR002199, Combined or Kabat definition

<400> SEQUENCE: 36

Gly Ile Arg Gly Ser Asp Gly Ser Thr Tyr Tyr Ala Asp Ser Val Lys
1 5 10 15

Gly

<210> SEQ ID NO 37
<211> LENGTH: 17
<212> TYPE: PRT
<213> ORGANISM: Artificial Sequence
<220> FEATURE:
<223> OTHER INFORMATION: VH2 HCDR2 of antibody PR002299, Combined or Kabat definition

<400> SEQUENCE: 37

Gly Ile Ser Glu Ser Gly Gly Ser Thr Tyr Tyr Ala Asp Ser Val Lys
1 5 10 15

Gly

<210> SEQ ID NO 38
<211> LENGTH: 19
<212> TYPE: PRT
<213> ORGANISM: Artificial Sequence
<220> FEATURE:
<223> OTHER INFORMATION: VH1 HCDR2 of antibody PR002299 or PR003178, Combined or Kabat definition

<400> SEQUENCE: 38

Arg Ile Arg Ser Lys Tyr Asn Asn Tyr Ala Thr Tyr Tyr Ala Asp Ser
1 5 10 15

Val Lys Asp

<210> SEQ ID NO 39
<211> LENGTH: 10
<212> TYPE: PRT
<213> ORGANISM: Artificial Sequence
<220> FEATURE:
<223> OTHER INFORMATION: VH2 HCDR3 of antibody PR002199, Chothia, Combined or Kabat definition

<400> SEQUENCE: 39

Gln Gly Glu Asn Asp Gly Pro Phe Asp His
1 5 10

<210> SEQ ID NO 40
<211> LENGTH: 12
<212> TYPE: PRT
<213> ORGANISM: Artificial Sequence
<220> FEATURE:
<223> OTHER INFORMATION: HCDR3 of antibody PR000274, Chothia, Combined or Kabat definition

<400> SEQUENCE: 40

Gly Ala Ile Tyr Asp Gly Tyr Asp Val Leu Asp Asn
1 5 10

<210> SEQ ID NO 41
<211> LENGTH: 13
<212> TYPE: PRT

```
<213> ORGANISM: Artificial Sequence
<220> FEATURE:
<223> OTHER INFORMATION: VH2 HCDR3 of antibody PR002299, Chothia,
      Combined or Kabat definition

<400> SEQUENCE: 41

Asp Leu Asp Asp Ile Leu Thr Gly Tyr Tyr Lys Asp Tyr
1               5                   10


<210> SEQ ID NO 42
<211> LENGTH: 14
<212> TYPE: PRT
<213> ORGANISM: Artificial Sequence
<220> FEATURE:
<223> OTHER INFORMATION: HCDR3 of antibody PR001046 or VH2 HCDR3 of
      antibody PR003178 , Chothia, Combined or Kabat definition

<400> SEQUENCE: 42

Arg Asn Tyr Asp Asp Thr Arg Gly Thr Asp Val Phe Asp Ile
1               5                   10


<210> SEQ ID NO 43
<211> LENGTH: 14
<212> TYPE: PRT
<213> ORGANISM: Artificial Sequence
<220> FEATURE:
<223> OTHER INFORMATION: VH1 HCDR3 of antibody PR002199, Chothia,
      Combined or Kabat definition

<400> SEQUENCE: 43

Asp Ser Arg Gly Tyr Gly Asp Tyr Arg Leu Gly Gly Ala Tyr
1               5                   10


<210> SEQ ID NO 44
<211> LENGTH: 14
<212> TYPE: PRT
<213> ORGANISM: Artificial Sequence
<220> FEATURE:
<223> OTHER INFORMATION: VH1 HCDR3 of antibody PR002299 or antibody
      PR003178, Chothia, Combined or Kabat definition

<400> SEQUENCE: 44

His Gly Asn Phe Gly Asn Ser Tyr Val Ser Trp Phe Ala Tyr
1               5                   10


<210> SEQ ID NO 45
<211> LENGTH: 214
<212> TYPE: PRT
<213> ORGANISM: Artificial Sequence
<220> FEATURE:
<223> OTHER INFORMATION: LC of antibody PR000274, Chothia definition

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95
```

-continued

```
Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 46
<211> LENGTH: 214
<212> TYPE: PRT
<213> ORGANISM: Artificial Sequence
<220> FEATURE:
<223> OTHER INFORMATION: LC of antibody PR002199, Chothia definition

<400> SEQUENCE: 46

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 47
```

-continued

<211> LENGTH: 215
<212> TYPE: PRT
<213> ORGANISM: Artificial Sequence
<220> FEATURE:
<223> OTHER INFORMATION: LC of antibody PR002299 or PR003178, Chothia definition

<400> SEQUENCE: 47

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Asp Lys Ala Ala Leu Thr Leu Leu Gly Ala
65                  70                  75                  80

Gln Pro Glu Asp Glu Ala Glu Tyr Phe Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 48
<211> LENGTH: 11
<212> TYPE: PRT
<213> ORGANISM: Artificial Sequence
<220> FEATURE:
<223> OTHER INFORMATION: VL LCDR1 of antibody PR000274, Chothia, Combined or Kabat definition

<400> SEQUENCE: 48

```
Ser Ala Ser Gln Asp Ile Ser Asn Tyr Leu Asn
1               5                   10
```

<210> SEQ ID NO 49
<211> LENGTH: 11
<212> TYPE: PRT
<213> ORGANISM: Artificial Sequence
<220> FEATURE:
<223> OTHER INFORMATION: VL LCDR1 of antibody PR002199, Chothia, Combined or Kabat definition

<400> SEQUENCE: 49

```
Arg Ala Ser Gln Ser Val Ser Ser Asn Leu Ala
1               5                   10
```

<210> SEQ ID NO 50
<211> LENGTH: 14
<212> TYPE: PRT
<213> ORGANISM: Artificial Sequence
<220> FEATURE:
<223> OTHER INFORMATION: VL LCDR1 of antibody PR002299 or antibody PR003178, Chothia, Combined or Kabat definition

<400> SEQUENCE: 50

Arg Ser Ser Thr Gly Ala Val Thr Thr Ser Asn Tyr Ala Asn
1 5 10

<210> SEQ ID NO 51
<211> LENGTH: 7
<212> TYPE: PRT
<213> ORGANISM: Artificial Sequence
<220> FEATURE:
<223> OTHER INFORMATION: VL LCDR2 of antibody PR000274, Chothia, Combined or Kabat definition

<400> SEQUENCE: 51

Tyr Thr Ser Asn Leu His Ser
1 5

<210> SEQ ID NO 52
<211> LENGTH: 7
<212> TYPE: PRT
<213> ORGANISM: Artificial Sequence
<220> FEATURE:
<223> OTHER INFORMATION: VL LCDR2 of antibody PR002199, Chothia, Combined or Kabat definition

<400> SEQUENCE: 52

Gly Ala Ser Thr Arg Ala Thr
1 5

<210> SEQ ID NO 53
<211> LENGTH: 7
<212> TYPE: PRT
<213> ORGANISM: Artificial Sequence
<220> FEATURE:
<223> OTHER INFORMATION: VL LCDR2 of antibody PR002299, or VL LCDR2 of PR003178, Chothia, Combined or Kabat definition

<400> SEQUENCE: 53

Gly Thr Asn Lys Arg Ala Pro
1 5

<210> SEQ ID NO 54
<211> LENGTH: 9
<212> TYPE: PRT
<213> ORGANISM: Artificial Sequence
<220> FEATURE:
<223> OTHER INFORMATION: VL LCDR3 of antibody PR000274, Chothia definitionVL LCDR3 of PR000274, Combined definitionVL LCDR3 of PR000274, Kabat definition

<400> SEQUENCE: 54

Gln Gln Tyr Arg Lys Leu Pro Trp Thr
1 5

<210> SEQ ID NO 55
<211> LENGTH: 9
<212> TYPE: PRT
<213> ORGANISM: Artificial Sequence
<220> FEATURE:
<223> OTHER INFORMATION: VL LCDR3 of antibody PR002199, Chothia, Combined or Kabat definition

<400> SEQUENCE: 55

Gln Gln Tyr Asn Asn Trp Pro Trp Thr
1               5

<210> SEQ ID NO 56
<211> LENGTH: 9
<212> TYPE: PRT
<213> ORGANISM: Artificial Sequence
<220> FEATURE:
<223> OTHER INFORMATION: VL LCDR3 of antibody PR002299 or antibody PR003178, Chothia, Combined or Kabat definition

<400> SEQUENCE: 56

Ala Leu Trp Tyr Ser Asn Leu Trp Val
1               5

<210> SEQ ID NO 57
<211> LENGTH: 119
<212> TYPE: PRT
<213> ORGANISM: Artificial Sequence
<220> FEATURE:
<223> OTHER INFORMATION: VH2 of antibody PR002199, Chothia definition

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Ala Pro Gly Lys Gly Pro Glu Trp Val
        35                  40                  45

Ser Gly Ile Arg Gly Ser Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Glu Asn Asp Gly Pro Phe Asp His Arg Gly Gln Gly
            100                 105                 110

Thr Leu Val Thr Val Ser Ser
        115

<210> SEQ ID NO 58
<211> LENGTH: 121
<212> TYPE: PRT
<213> ORGANISM: Artificial Sequence
<220> FEATURE:
<223> OTHER INFORMATION: VH of antibody PR000274, Chothia definition

<400> SEQUENCE: 58

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

-continued

```
Met Glu Leu Ser Ser Leu Arg Ser Glu Asp Thr Ala Val Tyr Tyr Cys
                85                  90                  95

Ala Arg Gly Ala Ile Tyr Asp Gly Tyr Asp Val Leu Asp Asn Trp Gly
            100                 105                 110

Gln Gly Thr Leu Val Thr Val Ser Ser
        115                 120
```

<210> SEQ ID NO 59
<211> LENGTH: 122
<212> TYPE: PRT
<213> ORGANISM: Artificial Sequence
<220> FEATURE:
<223> OTHER INFORMATION: VH2 of antibody PR001046 or PR003178, Chothia definition

<400> SEQUENCE: 59

```
Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Val Ser Asp Asn
            20                  25                  30

Tyr Met Thr Trp Val Arg Gln Ala Pro Gly Lys Gly Leu Glu Trp Val
        35                  40                  45

Ser Val Ile Phe Ser Gly Gly Asn Thr Tyr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Leu Tyr Tyr Cys Ala
                85                  90                  95

Arg Arg Asn Tyr Asp Asp Thr Arg Gly Thr Asp Val Phe Asp Ile Trp
            100                 105                 110

Gly Gln Gly Thr Met Val Thr Val Ser Ser
        115                 120
```

<210> SEQ ID NO 60
<211> LENGTH: 122
<212> TYPE: PRT
<213> ORGANISM: Artificial Sequence
<220> FEATURE:
<223> OTHER INFORMATION: VH2 of antibody PR002299, Chothia definition

<400> SEQUENCE: 60

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ile Trp Val Arg Gln Ala Pro Gly Lys Gly Leu Glu Trp Val
        35                  40                  45

Ser Gly Ile Ser Glu Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Val Lys Asp Leu Asp Asp Ile Leu Thr Gly Tyr Tyr Lys Asp Tyr Trp
            100                 105                 110

Gly Gln Gly Thr Leu Val Thr Val Ser Ser
        115                 120
```

<210> SEQ ID NO 61
<211> LENGTH: 123
<212> TYPE: PRT
<213> ORGANISM: Artificial Sequence
<220> FEATURE:
<223> OTHER INFORMATION: VH1 of antibody PR002199, Chothia definition

<400> SEQUENCE: 61

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser
        115                 120
```

<210> SEQ ID NO 62
<211> LENGTH: 125
<212> TYPE: PRT
<213> ORGANISM: Artificial Sequence
<220> FEATURE:
<223> OTHER INFORMATION: VH1 of antibody PR002299, Chothia definition

<400> SEQUENCE: 62

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 63
<211> LENGTH: 125
<212> TYPE: PRT
<213> ORGANISM: Artificial Sequence
<220> FEATURE:
<223> OTHER INFORMATION: VH1 of antibody PR003178, Chothia definition

<400> SEQUENCE: 63

```
Glu Val Gln Leu Val Glu Ser Gly Gly Gly Leu Val Gln Pro Gly Gly
1               5                   10                  15
```

```
Ser Leu Lys Leu Ser Cys Ala Ala Ser Gly Phe Thr Phe Ser Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125


<210> SEQ ID NO 64
<211> LENGTH: 107
<212> TYPE: PRT
<213> ORGANISM: Artificial Sequence
<220> FEATURE:
<223> OTHER INFORMATION: VL of antibody PR000274, Chothia definition

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95

Thr Phe Gly Gln Gly Thr Lys Leu Glu Ile Lys
            100                 105


<210> SEQ ID NO 65
<211> LENGTH: 107
<212> TYPE: PRT
<213> ORGANISM: Artificial Sequence
<220> FEATURE:
<223> OTHER INFORMATION: VL of antibody PR002199, Chothia definition

<400> SEQUENCE: 65

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
```

-continued

```
                85                  90                  95

Thr Phe Gly Gln Gly Thr Lys Val Glu Ile Lys
            100                 105


<210> SEQ ID NO 66
<211> LENGTH: 109
<212> TYPE: PRT
<213> ORGANISM: Artificial Sequence
<220> FEATURE:
<223> OTHER INFORMATION: VL of antibody PR002299 or antibody PR003178,
      Chothia definition

<400> SEQUENCE: 66

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Asp Lys Ala Ala Leu Thr Leu Leu Gly Ala
65                  70                  75                  80

Gln Pro Glu Asp Glu Ala Glu Tyr Phe Cys Ala Leu Trp Tyr Ser Asn
                85                  90                  95

Leu Trp Val Phe Gly Gly Gly Thr Lys Leu Thr Val Leu
            100                 105


<210> SEQ ID NO 67
<211> LENGTH: 5
<212> TYPE: PRT
<213> ORGANISM: Artificial Sequence
<220> FEATURE:
<223> OTHER INFORMATION: Synthesized

<400> SEQUENCE: 67

Gly Gly Gly Gly Ser
1               5


<210> SEQ ID NO 68
<211> LENGTH: 15
<212> TYPE: PRT
<213> ORGANISM: Artificial Sequence
<220> FEATURE:
<223> OTHER INFORMATION: Synthesized

<400> SEQUENCE: 68

Gly Gly Gly Gly Ser Gly Gly Gly Gly Ser Gly Gly Gly Gly Ser
1               5                   10                  15


<210> SEQ ID NO 69
<211> LENGTH: 20
<212> TYPE: PRT
<213> ORGANISM: Artificial Sequence
<220> FEATURE:
<223> OTHER INFORMATION: Synthesized

<400> SEQUENCE: 69

Gly Gly Gly Gly Ser Gly Gly Gly Gly Ser Gly Gly Gly Gly Ser Gly
1               5                   10                  15

Gly Gly Gly Ser
            20
```

ANTIBODY TARGETING BCMA, BISPECIFIC ANTIBODY, AND USE THEREOF

REFERENCE TO SEQUENCE LISTING

The Sequence Listing is submitted concurrently with the specification as an ASCII formatted text file via EFS-Web, with a file name of "17424-000114-US-NP_15_Jul_2025_revised_ST25", a creation date of Jul. 15, 2025, and a size of 61,536 bytes. The Sequence Listing filed via EFS-Web is part of the specification and is incorporated in its entirety by reference herein.

This application is a National Stage of International Application No. PCT/CN2020/118780, filed on Sep. 29, 2020, which claims priority to Chinese patent application 2019109413110, filed on 2019 Sep. 30. This content of which are incorporated herein by its entirety.

TECHNICAL FIELD

The present disclosure belongs to the field of biopharmaceuticals, and particularly relates to an antibody targeting BCMA, bispecific antibody and use thereof.

BACKGROUND

BCMA (B-cell maturation antigen, TNFRSF17, CD269) is a transmembrane protein belonging to the TNF receptor superfamily. As a non-glycosylated transmembrane protein, BCMA involved in B-cell maturation, growth and survival. BCMA is the receptor of two ligands of TNF superfamily: high affinity ligand APRIL (proliferation inducing ligand) and low affinity ligand BAFF (B cell activating factor). As a highly differentiated plasma cell-selective protein, the expression of BCMA is restricted to B-cell lineage, and is found mainly on plasma cells and plasma mother cells, and memory B-cells to a certain extent, but not on peripheral B-cells. BCMA is expressed in malignant plasma cells from patients with multiple myeloma (MM), supporting the growth and survival of multiple myeloma cells.

Multiple myeloma is the second most hematologic malignancy after non-Hodgkin's lymphoma, accounting for about 1% of all malignancies, 13% of hematologic malignancies, and 2% of deaths due to malignancies. Myeloma cells usually proliferate clonally in the bone marrow and the soft tissues of skeletal sponges, causing osteolytic bone destruction and poor healing mostly associated with anemia, renal failure and multiple damages caused by extramedullary infiltration of myeloma cells. As of 2006, the 5 annual relative productivity of MM is approximately 34%, and all therapies currently used for MM are non-curative. As an emerging target in multiple myeloma, BCMA antibodies can act on MM cells through multiple mechanisms. The research and development involving BCMA has focused on monoclonal antibodies, CAR-T therapies, ADCs, and bispecific antibody therapies.

The prior art antibody1 (hereinafter referred to as the positive control, and numbered PR000274 in the Examples) is the anti-BCMA antibody CA8-J6M0 hIgG1 from GlaxoSmithKline (GSK). At present, the antibody conjugated drug bellantamab mafodotin (CA8-J6M0-mcMMAF, GSK2857916) prepared by GSK based on the anti-BCMA antibody CA8-J6M0 has been used to treat different types of MM patients in a number of clinical trials. The sequence of this control antibody was derived from (Tabs-therapeutic Antibody database). Data from a small clinical study showed that the objective response rate (ORR) was 60% and the median progression free survival (PFS) was 12 months in 35 patients with over-pretreated (most patients had failed at least five therapy) relapsed or refractory (R/R) multiple myeloma (MM). In terms of safety, the most common side effects include corneal events, thrombocytopenia and anemia, all of which are associated with cytotoxic agents conjugated in ADC.

Currently, bispecific antibodies in clinical development include AMG-420 from Amgen, REGN-5458 from Regeneron, CC-93269 from Shinkee, JNJ-64007957 from Johnson & Johnson, and TNB383B from AbbVie. However, these bispecific antibodies also suffer from problems such as short half lives and cytokine release syndrome (CRS). The prior art antibody 2 (hereinafter referred to as the positive control 2, and numbered PR002199 in the Examples) is an anti-BCMA (TNB308902) x CD3 (TNB_F2B) bispecific antibody deriving from Teneobio's patent WO2018052503. Teneobio's TNB383B bispecific antibody for MM has entered clinical phase I in the 2019. The TNB383B uses a weakened CD3 antibody with attenuated cytokine release. However, TNB383B does not bind to CD3 and BCMA in cynomolgus monkeys and cannot be evaluated toxicologically in cynomolgus monkeys.

Therefore, there is an urgent need to develop safer and more effective monoclonal antibodies targeting BCMA and binding to BCMA of cynomolgus monkeys, as well as safer and more effective bispecific antibodies targeting both human BCMA and CD3 and binding to BCMA and CD3 of cynomolgus monkeys.

Content of the Present Invention

In order to solve the technical problems of the lack of safe and effective monoclonal antibodies targeting human BCMA and binding BCMA of cynomolgus monkeys, and the defect of bispecific antibodies targeting both human BCMA and CD3 and binding BCMA and CD3 of cynomolgus monkeys in the prior art, the present disclosure provides an antibody targeting BCMA, bispecific antibodies targeting BCMA and CD3, and uses thereof.

To solve the above-mentioned technical problems, the technical solution of the first aspect in the present disclosure is: an antibody targeting BCMA comprising two heavy chain variable regions, wherein the heavy chain variable region comprises HCDR1, HCDR2 and HCDR3 as shown in the amino acid sequences of SEQ ID NO: 22, SEQ ID NO: 33 and SEQ ID NO: 42, respectively; or, comprises HCDR1, HCDR2 and HCDR3 as shown in the amino acid sequences of SEQ ID NO: 26, SEQ ID NO: 37 and SEQ ID NO: 41, respectively. The BCMA antibody of the present disclosure has binding activity to human BMCA and cynomolgus monkey BCMA. The antibody is only half the size of conventional IgG antibodies, which can be used in developing bispecific antibody and solving the problems of light chain mismatch and heterodimerization.

In a preferred specific embodiment, the heavy chain variable region has amino acid sequences of SEQ ID NO: 59; or the heavy chain variable region has amino acid sequences of SEQ ID NO: 60 or mutant thereof; the mutant has an addition, substitution or deletion of one or more amino acids on the original amino acid sequence, maintaining or improving the binding capacity of the first protein functional region to the BCMA antigen. Preferably, the mutant has 80%, 85%, 90%, 95%, 96%, 97%, 98%, 99% or more of sequence identity to the amino acid sequence as shown in SEQ ID NO: 59, SEQ ID NO: 60.

In a preferred specific embodiment, the antibody targeting BCMA further comprises an Fc fragment. Thereby, the antibody targeting BCMA comprises two heavy chains. Preferably, the Fc fragment is an Fc fragment of hIgG1, hIgG2, hIgG3, hIgG4 or mutation thereof.

In a preferred specific embodiment, the heavy chain has an amino acid sequence of SEQ ID NO: 1, SEQ ID NO: 7 or SEQ ID NO: 8.

To solve the above-mentioned technical problem, the technical solution of the second aspect in the present disclosure is: a bispecific antibody, comprising a first protein functional region targeting BCMA and a second protein functional region targeting CD3, wherein, the first protein functional region comprises the heavy chain variable region of the antibody targeting BCMA of the technical solution in the first aspect; preferably, the two heavy chain variable regions are linked by (G4S)n, the n is a non-0 natural number, preferably 1-20; more preferably 3 or 4. The BCMAxCD3 bispecific antibody of the present disclosure is a unique BCMAxCD3 bispecific antibody with two sites for binding to BCMA, thereby improving the affinity and specificity of binding to BCMA on tumor cells; both protein functional regions of the bispecific antibody have good binding activity to cynomolgus monkey. The sequence G4S is numbered as SEQ ID NO: 67. When n is 3, the sequence (G4S)n is numbered as SEQ ID NO: 68. When n is 4, the sequence (G4S)n is numbered as SEQ ID NO: 69.

In a preferred specific embodiment, the second protein functional region comprises a heavy chain variable region and a light chain variable region, the heavy chain variable region has HCDR1, HCDR2 and HCDR3 with amino acid sequences of SEQ ID NO: 25, SEQ ID NO: 38 and SEQ ID NO: 44, respectively, and/or, the light chain variable region has LCDR1, LCDR2 and LCDR3 with amino acid sequences of SEQ ID NO: 50, SEQ ID NO: 53 and SEQ ID NO: 56, respectively.

Preferably, the heavy chain variable region of the second protein functional region has an amino acid sequence of SEQ ID NO: 63, SEQ ID NO: 62 or mutant thereof, and the light chain variable region has an amino acid sequence of SEQ ID NO: 66 or mutant thereof, and the mutant maintains or improves the binding of the second protein functional region to CD3. The bispecific antibody of the present disclosure optimizes the activity of the CD3 terminus, reduces the release of cytokines and reduces the toxicity of the BCMAxCD3 bispecific antibody.

In a preferred specific embodiment, the bispecific antibody further comprises a heavy chain constant region and a light chain constant region, preferably a human heavy chain constant region and a human light chain constant region, and the human light chain constant region is preferably a human λ or κ light chain constant region, and the human heavy chain constant region is preferably a heavy chain constant region of hIgG1, hIgG2, hIgG3 or hIgG4 or mutant thereof.

Preferably, the mutant of the human heavy chain constant region is selected from the group consisting of:

(1) L234A/L235A mutation;

(2) knob mutation T366W and hole mutations T366S, L368A and Y407V;

(3) knob mutation S354C and hole mutation Y349C;

More preferably, the first protein functional region comprises a heavy chain with an amino acid sequence of SEQ ID NO: 8 or SEQ ID NO: 7, and the second protein functional region comprises a heavy chain with an amino acid sequence of SEQ ID NO: 5 or SEQ ID NO: 4 and a light chain with an amino acid sequence of SEQ ID NO: 47. The bispecific antibody of the present disclosure has a human Fc fragment that retains the binding effect on FcRn and thus has a long half-life.

To solve the above-mentioned technical problem, the technical solution of the third aspect in the present disclosure is to provide an isolated nucleic acids encoding the antibody targeting BCMA according to the first aspect of the present disclosure or the bispecific antibody as described in the second aspect of the present disclosure.

To solve the above-mentioned technical problem, the technical solution of the fourth aspect in the present disclosure is to provide an expression vector comprising the isolated nucleic acids according to the third aspect of the present disclosure.

To solve the above-mentioned technical problem, the technical solution of the fifth aspect in the present disclosure is to provide a host cell comprising an expression vector of the fourth aspect of the present disclosure; preferably, the host cell is a prokaryotic cell or a eukaryotic cell.

To solve the above-mentioned technical problem, the technical solution of the sixth aspect in the present disclosure is to provide antibody drug conjugate comprising the antibody targeting BCMA of the first aspect of the present disclosure or a bispecific antibody of the second aspect of the present disclosure, and a cytotoxic agent.

To solve the above-mentioned technical problem, the technical solution of the seventh aspect in the present disclosure is to provide a pharmaceutical composition comprising the antibody targeting BCMA of the first aspect of the present disclosure, the bispecific antibody of the second aspect of the present disclosure, or the antibody drug conjugate of the sixth aspect of the present disclosure, and a pharmaceutically acceptable carrier.

To solve the above-mentioned technical problem, the technical solution of the eighth aspect in the present disclosure is to provide a use of the antibody targeting BCMA of the first aspect of the present disclosure, the bispecific antibody of the second aspect of the present disclosure, the antibody drug conjugate of the sixth aspect of the present disclosure, or a pharmaceutical composition of the seventh aspect of the present disclosure in the preparing a medicament for treating and/or preventing cancer.

Furthermore, in order to solve the above-mentioned technical problems, the technical solution of the ninth aspect of the present disclosure provides a kit combination comprising kit A and kit B; the kit A comprises the antibody targeting BCMA of the first aspect in the present disclosure, the bispecific antibody of the second aspect in the present disclosure, the host cell of the fifth aspect in the present disclosure, the antibody drug conjugate of the sixth aspect in the present disclosure, or the pharmaceutical composition of the seventh aspect in the present disclosure; kit B comprises other antibodies, bispecific antibodies, host cells or pharmaceutical compositions, and the other antibodies, bispecific antibodies, host cells or pharmaceutical compositions targeting CD3, BCMA or other targets. Kit A and kit B can be used with no particular order, or kit A is used before kit B, or kit B is used before kit A.

The antibody targeting BCMA of the technical solution in the first aspect of the present disclosure, the bispecific antibody of the technical solution in the second aspect of the present disclosure, the host cell of the technical solution in the fifth aspect of the present disclosure, the antibody drug conjugate of the technical solution in the sixth aspect of the present disclosure, or the pharmaceutical composition of the technical solution in the seventh aspect of the present disclosure may be administered to a patient for the treatment of a relevant tumor.

On the basis of common knowledge in the art, each of the above preferred conditions can be combined in any way to obtain each preferred example of the present disclosure.

The reagents and raw materials used in the present disclosure are all commercially available.

The positive and progressive effects of the present disclosure are: 1. The BCMA antibody in the present disclosure is a novel full human antibody comprising only "heavy chain" with binding activity to human BMCA and cynomolgus monkey BCMA. The BCMA heavy chain antibody is only half the size of conventional IgG antibodies. The absence of a light chain in the antibody makes it possible to use in preparing bispecific antibodies and to solve the problems of light chain mismatch and heterodimerization.

2. The BCMAxCD3 bispecific antibody in the present disclosure: a. is a unique BCMAxCD3 bispecific antibody with two sites to bind BCMA, thus improves the affinity and specificity of binding to BCMA on tumor cells; b. has a bispecific antibody structure with a human Fc fragment that retains the binding effect of Fc to FcRn, thus having a long half-life; c. optimizes the activity of the CD3 terminus, reduces cytokine release, and decreases the toxicity of the BCMAxCD3 bispecific antibody; d. the BCMA terminus and CD3 terminus of the antibody have good binding activity to that of cynomolgus monkey.

BRIEF DESCRIPTION OF THE DRAWINGS

FIGS. 4A-4C show in vitro binding capacity assay of BCMA x CD3 bispecific antibody on HEK293T cell strain overexpressing human and cynomolgus monkey BCMA with FACS.

FIGS. 7A-7E show in vitro killing experiment and cytokine release of BCMAxCD3 bispecific antibody against cell line RPMI8226 low expressing BCMA.

FIGS. 11A-11E show detection for affinity of PR003178 to human CD3e/g recombinant protein, cynomolgus monkey CD3e/g recombinant protein, human BCMA recombinant protein and cynomolgus monkey BCMA recombinant protein with BIACORE.

DETAILED DESCRIPTION OF THE PREFERRED EMBODIMENT

Figure 1A:
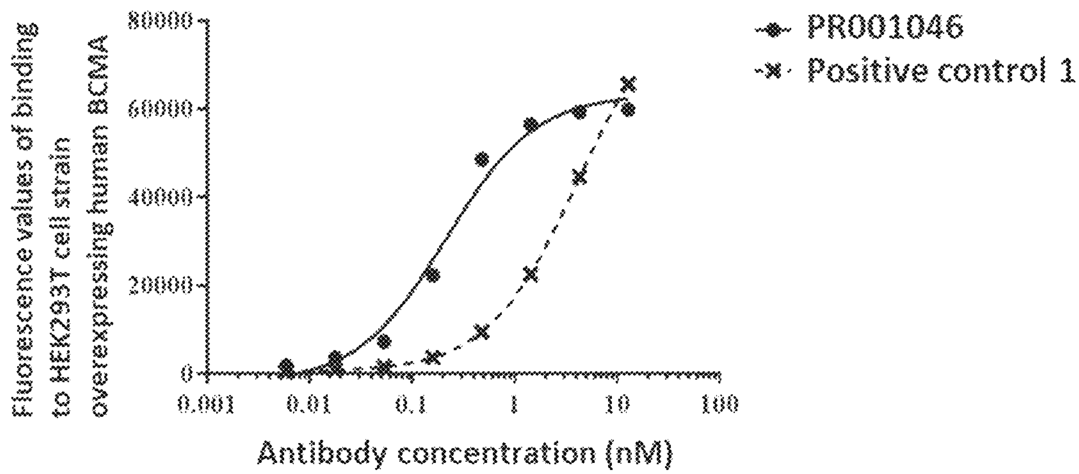
FIGS. 1A-1D show the binding capacity assay of anti-human BCMA HCAb monoclonal antibody at cellular level with FACS.
Figure 1B:
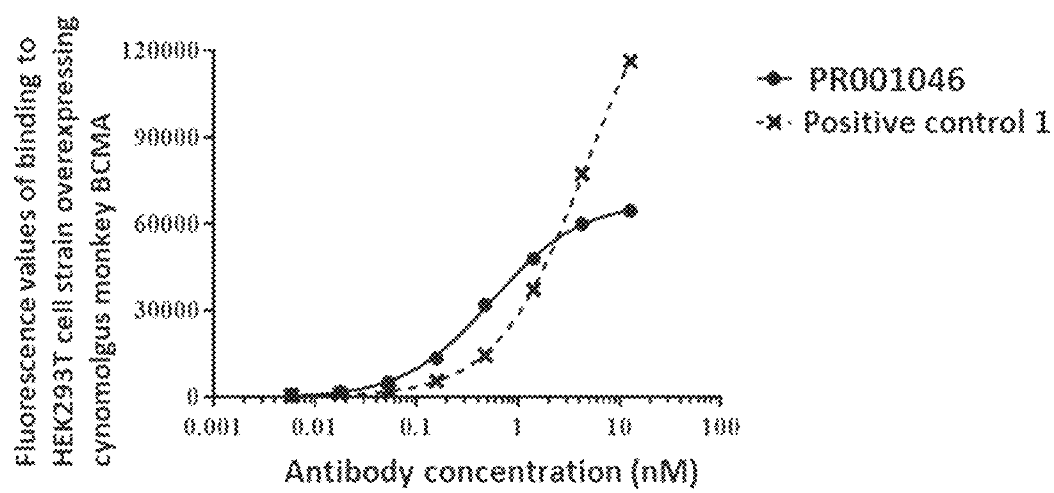
Figures 1C, 1D:
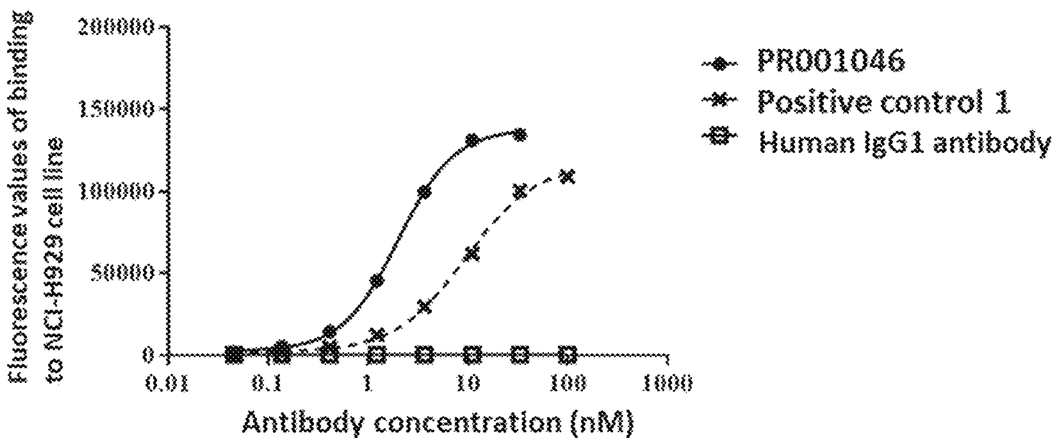

The present disclosure will be further illustrated by the following examples but the present disclosure is not limited to the scope of examples thereto. The experimental methods for which specific conditions are not indicated in the following examples shall be selected according to conventional methods and conditions, or according to the specification of commodity.

In this application, the term "antibody" generally refers to a protein comprising an antigen-binding portion, and optionally a scaffold or backbone portion that allows the antigen-binding portion to apply a conformation that facilitates the binding of an antibody to an antigen. An antibody may typically comprise an antibody light chain variable region (VL), an antibody heavy chain variable region (VH), or both. For example, "heavy chain antibody" in the present application comprises a VH region without a VL region. A VH or VL region may be further divided into a hypervariable region called complementarity determining region (CDR), and a more conserved region called framework region (FR) where the CDRs are scattered. Each VH or VL may consist of three CDRs and four FRs, which can be arranged in the following order from amino terminus to carboxyl terminus: FR1, CDR1, FR2, CDR2, FR3, CDR3 and FR4. The variable regions of a heavy chain and a light chain comprise binding domains that interact with an antigen. The examples of an antibody include, but not limited to, full-length antibody, heavy chain antibody (HCAb), antigen-binding fragment (Fab, Fab', F(ab)2, Fv fragment, F(ab')2, scFv, di-scFv and/or dAb), immuno-conjugate, multispecific antibody (e.g., bispecific antibody), antibody fragment, antibody derivative, antibody analog, or fusion protein, etc, as long as they show the desired antigen-binding activity.

In this application, the term "variable" generally refers to the fact that certain portions of the sequence of a variable domain in an antibody varies intensively, which forms the binding and specificity of various specific antibodies to their specific antigen. However, the variability is not distributed uniformly in the entire variable region of an antibody. The variability is centralized in three segments of the variable regions of a light chain and a heavy chain, called CDR or hypervariable region (HVR), with a FR being the more highly-conserved portions of the variable domain. Each of the variable domains of natural heavy chain and light chains comprises four FRs, most of which are using β-fold conformation and linked by three CDRs, forming a loop linkage and being part of a β-fold structure in some cases. The CDRs in each chain are closely adjacent to each other through the FRs and are forming an antigen-binding site of an antibody together with the CDRs from the other chain. The constant regions are not directly involved in antibody-antigen binding, but they exhibit different effector functions, such as participating in antibody-dependent cytotoxicity of the antibody.

In the present art, the CDR of an antibody can be defined by various methods, such as Kabat definition rule (see Kabat et al., Sequences of Proteins of Immunological Interest, Fifth Edition, National Institutes of Health, Bethesda, MD (1991)) based on sequence variability and Chothia definition rule based on the regional position of a structural loop (see Al-Lazikani et al., J Mol Biol 273:927-48, 1997). In the present application, Combined definition rule incorporating Kabat definition and Chothia definition was also used to determine amino acid residues in the sequences of a variable domain and a full-length antibody (Table1).

TABLE 1

| Definition method for the CDRs of the antibody in the present application (available at bioinf.org.uk/abs) | | | |
|---|---|---|---|
| CDR region | Kabat definition | Chothia definition | Combined definition |
| LCDR1 | L24 - - - L34 | L24 - - - L34 | L24 - - - L34 |
| LCDR2 | L50 - - - L56 | L50 - - - L56 | L50 - - - L56 |
| LCDR3 | L89 - - - L97 | L89 - - - L97 | L89 - - - L97 |
| HCDR1 | H31 - - - H35 | H26 - - - H32 | H26 - - - H35 |
| HCDR2 | H50 - - - H65 | H52 - - - H56 | H50 - - - H65 |
| HCDR3 | H95 - - - H102 | H95 - - - H102 | H95 - - - H102 |

Wherein, Laa-Lbb can refer to the amino acid sequence from aa position (Chothia numbering rule) to bb position (Chothia numbering rule) started from N-terminal of the light chain of an antibody; Haa-Hbb can refer to the amino acid sequence from aa position (Chothia numbering rule) to bb position (Chothia numbering rule) started from N-terminal of the heavy chain of an antibody. For example, L24-L34 can refer to the amino acid sequence from position 24 to position 34 started from N-terminal of the light chain of an antibody according to Chothia numbering rule; H26-H32 can refer to the amino acid sequence from position 26 to position 32 started from N-terminal of the heavy chain of an antibody according to Chothia numbering rule.

The effector functions such as ADCC and CDC mediated by Fc domain of an antibody have significant biological functions, and different IgG isoforms have different ADCC or CDC functions. For example, IgG1 and IgG3 have relatively strong ADCC and CDC effects, while IgG2 and IgG4 have relatively weak effects. In addition, the original effector function of Fc can also be modulated by amino acid mutations or modifications to alter the binding capacity of Fc to the Fc receptor. For example, "LALA" double mutant (L234A/L235A) in IgG1 can significantly decrease its affinity to FcγRIIIA (CD16A) and thus decreases the ADCC effect. In addition, P329G mutation can significantly decrease the binding to multiple Fc7 receptors (see Schlothauer T, Herter S, Koller C F, Grau-Richards S, Steinhart V, Spick C, Kubbies M, Klein C, Umana P, Mössner E. Novel human IgG1 and IgG4 Fc-engineered antibodies with completely abolished immune effector functions. Protein EngDes Sel. 2016 October; 29(10):457-466. doi: 10.1093/protein/gzw040. Epub 2016 Aug. 29. PubMed PMID: 27578889). In the application, in order to decrease the binding of BCMAxCD3 bispecific antibodies to Fcγ receptors, "LALA" double mutant (L234A/L235A) or "LALAPG" triple mutant (L234A/L235A/P329G) was introduced to the Fc of these antibodies.

Example 1. Mouse Immunization and Obtaining Anti-BCMA Antibody Molecules

BCMA antigens can be used to immunize experimental animals to obtain antibody molecules specifically binding to BCMA, and the experimental animals can be mice, rats, rabbits, sheep, camels, etc. Generally, the antibody molecules obtained are non-human origin. After obtaining non-human antibodies, these molecules need to be humanized using antibody engineering techniques to reduce immunogenicity and improve drug-forming properties. However, the humanization process of antibodies is complicated technically as the humanized molecules often have decreased affinity to the antigen. On the other hand, advances in transgenic technology have made it possible to breed genetically engineered mice carrying a human immunoglobulin immune repertoire without its endogenous murine immune repertoire. The antibody produced by this transgenic mouse has a full human sequence, so there is no need for further humanization, which greatly improves the development efficiency of therapeutic antibody. Harbour HCAb mice (Harbour Antibodies BV, WO 2002/085945 A3) are transgenic mice that carry a human immunoglobulin immune repertoire, and are capable of producing a novel only "heavy chain" antibody that is half the size of conventional IgG antibodies. The antibodies produced therefrom Harbour HCAb mice only have a "heavy chain" variable domain of a human antibody and a murine Fc constant domain. The absence of a light chain in this antibody almost makes it a solution to problems of light chain mismatch and heterodimerization, allowing this technology platform to develop products that are difficult to achieve with traditional antibody platforms.

1.1 Immunization of Mice with BCMA Antigen

Harbour HCAb mice were immunized with multiple rounds of a soluble recombinant human BCMA-ECD-Fc fusion protein. The antigen protein was mixed with an immune adjuvant to form an immunogenic reagent, which is then injected subcutaneously through groin or intraperitoneally. In each round of immunization, each mouse received a total injection dose of 100 μL. In the first round of immunization, each mouse received an immunization with an immunogenic reagent prepared by mixing 50 μg of antigen protein (recombinant human BCMA-ECD-Fc, ACRO, Cat. BC7-H82F0) and complete Freund's adjuvant (Sigma, #F5881) at a volume ratio of 1:1. In each subsequent booster of immunization, each mouse received an immunization with an immunogenic reagent prepared by mixing 25 μg of antigen protein and Sigma Adjuvant System adjuvant (Sigma, #S6322). The interval between each round of booster immunization was at least two weeks, and usually the immunization had no more than five rounds of booster immunization. The immunization time was day 0, 14, 28, 42, 56 and 70 the murine serum antibody titers were detected on days 49 and 77. The final booster immunization was performed at a dosage of 25 μg of antigen protein per mouse five days before the isolation of spleen B cells from HCAb mice.

1.2 Obtaining HCAb Monoclonal and Antibody Sequences

When the murine serum antibody titer specific to BCMA reached a certain level, murine spleen cells were removed to isolate B cells, and CD138-positive plasma cells and BCMA antigen-positive B cell populations were sorted by BD FACS AriaII Cell Sorter. RNA was extracted, and reverse transcripted to cDNA, then the human VH gene was amplified by PCR. The amplified VH gene fragment was constructed into the mammalian cell expression plasmid pCAG vector encoding the Fc domain sequence in the heavy chain of a human IgG1 antibody. The plasmid was transfected into mammalian host cells (e.g. human embryonic kidney cell HEK293) for expression. The antibody supernatant of HCAb expressed was screened by Mirrorball with recombinant human BCMA-Fc and Avitag recombinant protein (ACRO, Cat. Bc7-H82F0). The binding capacity of the Mirrorball-positive monoclonal antibodies obtained to cells of HEK293T cell strain overexpressing human BCMA (HEK293T/huBCMA, Beijing KangYuan), HEK293T cell strain overexpressing cynomolgus monkey BCMA (HEK293T/cynoBCMA, Beijing KangYuan) and NCI-H929 cell line highly expressing human BCMA (ATCC® CRL-9068™) were further identified by FACS. The clone number of the positive clone obtained by screening is HBM1005P63B7, hereafter numbered PR001046. The nucleotide sequence encoding the variable domain of the antibody molecule and corresponding amino acid sequence were obtained by using conventional sequencing methods. In the present example, the sequence of the variable domain of the anti-BCMA monoclonal antibody molecule obtained from immunized Harbour HCAb mice was a human antibody sequence.

Table 2 lists the amino acid sequences of the variable domain and full length of the heavy chain, and the amino acid sequences of the CDRs defined according to Combined definition rule of the BCMA antibody in this example. See the sequencing list for the amino acid sequences of the CDRs defined according to other rules for the antibodies of the present disclosure.

TABLE 2

Amino acid sequences associated with anti-BCMA HCAb antibodies

| PR001046 | Amino acid sequence and sequence id number |
|---|---|
| Heavy chain sequence of PR001046 | EVQLVETGGGLIQPGGSLRLSCAASGFTVSDNYMTWVRQ APGKGLEWVSVIFSGGNTYYADSVKGRFTISRDNAKNTLY LQMNSLRAEDTALYYCARRNYDDTRGTDVFDIWGQGTM VTVSSEPKSCDKTHTCPPCPAPELLGGPSVFLFPPKPKDTL MISRTPEVTCVVVDVSHEDPEVKFNWYVDGVEVHNAKTK PREEQYNSTYRVVSVLTVLHQDWLNGKEYKCKVSNKALP APIEKTISKAKGQPREPQVYTLPPSREEMTKNQVSLTCLVK GFYPSDIAVEWESNGQPENNYKTTPPVLDSDGSFFLYSKLT VDKSRWQQGNVFSCSVMHEALHNHYTQKSLSLSPGK (SEQ ID NO: 1) |
| Heavy chain variable region sequence of PR001046 | EVQLVETGGGLIQPGGSLRLSCAASGFTVSDNYMTWVRQ APGKGLEWVSVIFSGGNTYYADSVKGRFTISRDNAKNTLY LQMNSLRAEDTALYYCARRNYDDTRGTDVFDIWGQGTM VTVSS (SEQ ID NO: 59) |
| PR001046 VH CDR1 (Combined) | GFTVSDNYMT (SEQ ID NO: 22) |
| PR001046 VH CDR2 (Combined) | VIFSGGNTYYADSVKG (SEQ ID NO: 33) |
| PR001046 VH CDR3 (Combined) | RNYDDTRGTDVFDI (SEQ ID NO: 42) |

1.3 Preparation of Anti-BCMA Full Human Recombinant Antibody

Plasmids encoding the heavy chain of antibody PR001046 were transfected into mammalian host cells (e.g. human embryonic kidney cell HEK293) to obtain purified anti-BCMA recombinant heavy chain antibodies using conventional recombinant protein expression and purification techniques. Specifically, HEK293 cells were cultured for expansion in FreeStyle™ F17 Expression Medium (Thermo, A1383504). Prior to starting transient transfection, the cell concentration was adjusted to $6\times10^5$ cells/ml. The cells were incubated at 37° C., 8% $CO_2$ in a shaker for 24 hours until the cell concentration reached $1.2\times10^6$ cells/ml. 30 ml of cultured cells was prepared, and then 30 μg of plasmids encoding PR001046 heavy chain described above was dissolved in 1.5 ml Opti-MEM reduced serum medium (Thermo, 31985088), and then 1.5 ml of Opti-MEM was taken to dissolve 120 μl of 1 mg/ml PEI (Polysciences, Inc, Cat #23966-2) and leave aside for 5 min. PEI was added slowly to the plasmids and incubated for 10 min at room temperature. The mixture of PEI and plasmids was dropped slowly into the cells with the culture flask shaking, and the cells were incubated at 37° C., 8% $CO_2$ in a shaker for 5 days. Cell viability was observed after 5 days. The cultures were collected and centrifuged at 3300 G for 10 minutes for the supernatant; then the supernatant was subject to high speed centrifugation to remove impurities. Gravity columns (Bio-Rad, #7311550) containing MabSelect® (GE Healthcare Life Science, Cat #71-5020-91 AE) were equilibrated with PBS (pH 7.4) and washed with 2-5 folds of column volume. The supernatant sample was subject to column chromatography. The columns were washed with 5-10 folds of column volume of PBS. The target protein was then eluted with 0.1 M glycine (pH 3.5), and adjusted to neutral with Tris-HCl (pH 8.0), and finally the solution was concentrated and exchanged with PBS buffer by concentration using ultrafiltration tubes (Millipore, UFC901024). The purified anti-BCMA heavy chain antibody solution was obtained.

The following table shows the sequences of light chain and heavy chain, variable region of the light chain and the heavy chain, and CDRs defined according to Combined definition rule of positive control 1, i.e., the full-length antibody PR000274.

TABLE 3

Amino acid sequences associated with full human recombinant antibody

| PR000274 | Amino acid sequences and sequence id number |
|---|---|
| heavy chain sequence of PR000274 | QVQLVQSGAEVKKPGSSVKVSCKASGGTFSNYWMHWVRQ APGQGLEWMGATYRGHSDTYYNQKFKGRVTITADKSTSTA YMELSSLRSEDTAVYYCARGAIYDGYDVLDNWGQGTLVT |

TABLE 3-continued

| Amino acid sequences associated with full human recombinant antibody | |
|---|---|
| PR000274 | Amino acid sequences and sequence id number |
| | VSSASTKGPSVFPLAPSSKSTSGGTAALGCLVKDYFPEPVTV SWNSGALTSGVHTFPAVLQSSGLYSLSSVVTVPSSSLGTQT YICNVNHKPSNTKVDKKVEPKSCDKTHTCPPCPAPELLGGP SVFLFPPKPKDTLMISRTPEVTCVVVDVSHEDPEVKFNWYV DGVEVHNAKTKPREEQYNSTYRVVSVLTVLHQDWLNGKE YKCKVSNKALPAPIEKTISKAKGQPREPQVYTLPPSREEMTK NQVSLTCLVKGFYPSDIAVEWESNGQPENNYKTTPPVLDSD GSFFLYSKLTVDKSRWQQGNVFSCSVMHEALHNHYTQKSL SLSPGK (SEQ ID NO: 2) |
| Heavy chain variable region sequence of PR000274 | QVQLVQSGAEVKKPGSSVKVSCKASGGTFSNYWMHWVRQ APGQGLEWMGATYRGHSDTYYNQKFKGRVTITADKSTSTA YMELSSLRSEDTAVYYCARGAIYDGYDVLDNWGQGTLVT VSS (SEQ ID NO: 58) |
| PR000274 VH CDR1 (Combined) | GGTFSNYWMH (SEQ ID NO: 21) |
| PR000274 VH CDR2 (Combined) | ATYRGHSDTYYNQKFKG (SEQ ID NO:34) |
| PR000274 VH CDR3 (Combined) | GAIYDGYDVLDN (SEQ ID NO: 40) |
| Light chain sequence of PR000274 | DIQMTQSPSSLSASVGDRVTITCSASQDISNYLNWYQQKPG KAPKLLIYYTSNLHSGVPSRFSGSGSGTDFTLTISSLQPEDFA TYYCQQYRKLPWTFGQGTKLEIKRTVAAPSVFIFPPSDEQL KSGTASVVCLLNNFYPREAKVQWKVDNALQSGNSQESVTE QDSKDSTYSLSSTLTLSKADYEKHKVYACEVTHQGLSSPVT KSFNRGEC (SEQ ID NO: 45) |
| Light Chain Variable region Sequence of PR000274 | DIQMTQSPSSLSASVGDRVTITCSASQDISNYLNWYQQKPG KAPKLLIYYTSNLHSGVPSRFSGSGSGTDFTLTISSLQPEDFA TYYCQQYRKLPWTFGQGTKLEIK (SEQ ID NO: 64) |
| PR000274 VL CDR1 (Combined) | SASQDISNYLN (SEQ ID NO: 48) |
| PR000274 VL CDR2 (Combined) | YTSNLHS (SEQ ID NO: 51) |
| PR000274 VL CDR3 (Combined) | QQYRKLPWT (SEQ ID NO: 54) |

Example 2. Binding Capacity Assay of Anti-Human BCMA HCAb Monoclonal Antibody at Cellular Level with FACS This example was conducted to study the binding activity of anti human BCMA HCAb monoclonal antibodies to human and cynomolgus monkey BCMA in vitro. HEK293T cell strain (HEK293T/huBCMA, Beijing Kang yuan) overexpressing human BCMA, HEK293T cell strain (HEK293T/cynoBCMA, Beijing Kang yuan) overexpressing cynomolgus monkey BCMA and NCI-H929 cell line (ATCC© CRL-9068™) highly expressing human BCMA were used for antibody binding assay at cellular level. Briefly, HEK293T/huBCMA cells and HEK293T/cynoBCMA cells were digested and resuspended with DMEM complete medium, and NCI-H929 cell suspensions were collected by resuspension with DMEM complete medium. The density of the three cells was adjusted to $1\times10^6$ cells/mL, respectively. The cells were inoculated at 100 μL cells/well in 96 well V-bottom plates (Corning, Cat #: 3894), followed by the addition of test antibodies at 100 μL/well, which is gradient diluted at 3 folds of the concentration with 2 folds of the final concentration. Cells were incubated at 4° C. for 1 hours in the dark. Afterwards, the cells were washed twice with 100 μL/well of pre-cooled PBS, centrifuged at 500 g for 5 min at 4° C. and followed by discarding the supernatant. Fluorescent secondary antibody (Alexa Fluor® 488-conjugated AffiniPure Goat Anti-Human IgG, Fcγ Fragment Specific, Jackson, Cat #:109-545-06, 1:500 dilution) was added at 100 μL/well and incubated for 30 min at 4° C. in the dark. Cells were washed twice with 100 μL/well of pre-cooled PBS, centrifuged at 500 g, 4° C. for 5 min, and followed by discarding the supernatant. Finally, the cells were resuspended with 200 μL/well of pre-cooled PBS and the fluorescent luminescence signal values were read by using BD FACS CANTOII.

As shown in FIGS. 1A-1D, the binding capacity of the anti-human BCMA HCAb monoclonal antibody PR001046 to the HEK293T cell strain overexpressing human BCMA (A), the HEK293T cell strain overexpressing cynomolgus monkey BCMA (B) and the cell line NCI-H929 (C) highly expressing human BCMA were all better than positive control 1 (PR000274). Specifically, the EC50 of the binding curve of PR001046 was lower than that of positive control 1, see FIG. 1D for the specific maximum fluorescence values and EC50.

Example 3. Blockage Assay of Anti-Human BCMA HCAb Monoclonal Antibody to the Binding of Human BCMA with Ligand BAFF Protein with ELISA This example was conducted to evaluate the blockage ability of anti-human BCMA HCAb monoclonal antibody to the binding of human BCMA (ACRO, BCA-H522y-100 μg) with ligand BAFF protein (ACRO, BAF-H5248-50 μg). The BAFF protein was biotinylated by using a biotinylation kit (ThermoFisher, A39257, EZ-Link® Sulfo-NHS-LC-Biotin) according to the instructions. The plates (Corning, Cat #: 9018) were coated with 1 μg/mL of human BCMA protein with Fc Tag (ACRO, Cat #: BC7-H5254) overnight. The plates were washed for 3 times with PBST, added with 2% BSA and then sealed at room temperature for 1 hour. The plates were washed with PBST for 3 times, and added with test antibody gradient diluted at 3 folds concentration 100 μL/well, with an initial concentration of 50 nM. After being incubated for 1 h, the supernatant was discarded and 0.5 μg/mL of biotinylated human BAFF protein (prepared according to conventional methods in the art) was added to the plates at 100 μL/well. The plates were incubated at room temperature for 1 h and discarded the supernatant. Streptavidin-coupled HRP (Bio-RAD, Cat #: 1610380) with 1:4000 diluted was added at 100 μL/well. The plates were incubated for 1 h at room temperature and washed with PBST for 3 times. TBM was added at 100 μL/well for color developing and the reaction was terminated 15 min later by adding termination solution. OD450 values were read by using Enspire (Perkin Elmer).

Figures 2A, 2B:
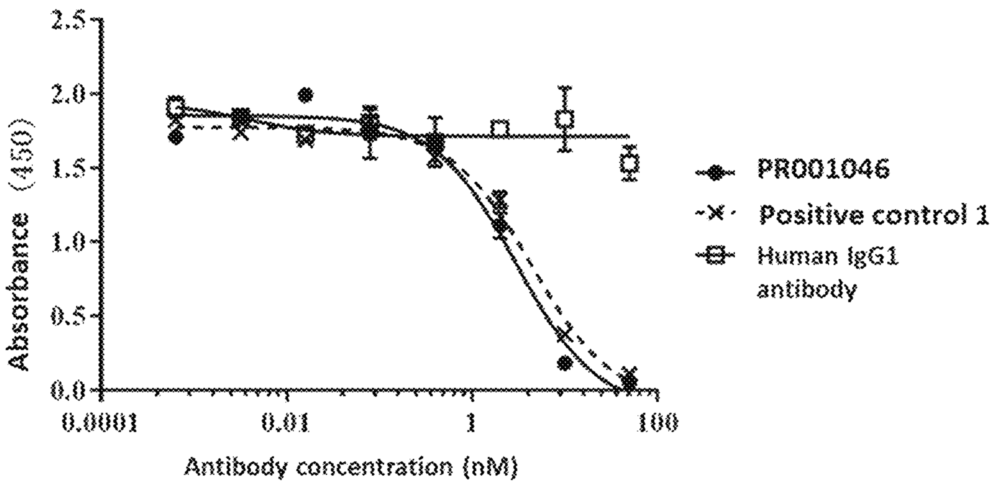
FIGS. 2A and 2B show the blockage assay of anti-human BCMA HCAb monoclonal antibody to the binding of human BCMA with ligand BAFF protein with ELISA.

As shown in FIG. 2A, anti-human BCMA HCAb monoclonal antibody PR001046 has the ability to block the binding of human BCMA with its ligand BAFF protein comparable to that of positive control 1 antibody. The specific IC50 values is shown in the FIG. 2B.

Example 4. Humanization of CD3 Antibody

Anti-CD3 antibody is an important component in the construction of T-Cell Engager Bispecific Antibody (T-Cell Engager Bispecific Antibody). Humanization was performed on the known murine antibody SP34 binding to human CD3e (CD3 epsilon single subunit or complex containing CD3e). As is described in WO2017084495A1 (Jiangsu Hengrui) or CN104136610B (Chugai Sangyo Co., Ltd.), the modification is briefly described as follows:

This example uses a "CDR transplantation" method for sequence humanization, that is, the VH CDRs of a murine antibody are transplanted to the VH framework region of a human antibody, and the VL CDRs of the murine antibody are transplanted to the VL framework region of the human antibody. The sequence of the framework region in VH or VL of human antibody can be derived from human germline gene sequence, or antibody sequences after V (D) J rearrangement, or the consensus sequence of a specific VH or VL gene family of human antibody. In this example, the frame region sequence provided by the human germline gene sequence was used as the humanized template sequence, that is, the human germline V gene fragment provides the sequence of frame regions FR1, FR2 and FR3, and the human germline J gene fragment provides the sequence of frame region FR4. Finally, humanized variable region (VH or VL) sequences were constructed in the order of (human) FR1-(murine) CDR1-(human) FR2-(murine) CDR2-(human) FR3-(murine) CDR3-(human) FR4.

In this example, the sequence of human germline V gene fragment IGHV3-73*01 or human germline V gene fragment IGHV3-23*01 combined with human germline J gene fragment IGHJ1*01 is used as a humanized template to provide a frame region sequence. And amino acid mutation at one or more sites was introduced at position 30, 73, 76, 78, 93 or 94 (according to Chothia numbering rules) to obtain various different VH variant sequences.

In this example, the sequence of the human germline V gene fragment IGLV7-46*02 combined with the sequence of the human germline J gene fragment IGLJ2*01 or the sequence of the human germline V gene fragment IGKV1-39*01 combined with the sequence of the human germline J gene fragment IGKJ4*01 is used as a humanized template to provide the frame region sequence. And amino acid mutation at none or more sites was introduced at position 2, 36, 46, 49, 66, 69, 71 or 87 (according to Chothia numbering rules) to obtain various different VL variant sequences. The following table 4 shows amino acid sequence of one of the CD3 antibodies, the sequences of the light chain (LC) and the heavy chain (hereinafter, the heavy chain and heavy chain variable region of the CD3 antibody of the present disclosure are referred to as HC1 and VH1 in the bispecific antibody, respectively) of this antibody and the heavy chain (hereinafter, the heavy chain and heavy chain variable region of the BCMA antibody of the present disclosure are referred to as HC2 and VH2 in the bispecific antibody, respectively) sequence of the BCMA antibody of the present disclosure will form the bispecific antibodies PR003178 and PR002299 (see Example 5 for the detailed construction method).

TABLE 4

| Amino acid sequences of the obtained CD3 antibodies<br>Sequence information of CD 3antibody used for PR003178 | |
|---|---|
| sequence of PR003178 HC1 | EVQLVESGGGLVQPGGSLKLSCAASGFTFSTYAMNWVRQASGK GLEWVGRIRSKYNNYATYYADSVKDRFTISRDDSKNTAYLQMNS LKTEDTAVYYCTRHGNFGNSYVSWFAYWGQGTLVTVSSASTKG PSVFPLAPSSKSTSGGTAALGCLVKDYFPEPVTVSWNSGALTSGV HTFPAVLQSSGLYSLSSVVTVPSSSLGTQTYICNVNHKPSNTKVDK KVEPKSCDKTHTCPPCPAPEAAGGPSVFLFPPKPKDTLMISRTPEV TCVVVDVSHEDPEVKFNWYVDGVEVHNAKTKPREEQYNSTYRV VSVLTVLHQDWLNGKEYKCKVSNKALPAPIEKTISKAKGQPREP QVYTLPPCREEMTKNQVSLWCLVKGFYPSDIAVEWESNGQPENN YKTTPPVLDSDGSFFLYSKLTVDKSRWQQGNVFSCSVMHEALHN HYTQKSLSLSPGK (SEQ ID NO: 5) |

TABLE 4-continued

| Amino acid sequences of the obtained CD3 antibodies Sequence information of CD 3antibody used for PR003178 | |
|---|---|
| sequence of PR003178 VH1 | EVQLVESGGGLVQPGGSLKLSCAASGFTFSTYAMNWVRQASGKGLEWVGRIRSKYNNYATYYADSVKDRFTISRDDSKNTAYLQMNSLKTEDTAVYYCTRHGNFGNSYVSWFAYWGQGTLVTVSS (SEQ ID NO: 63) |
| sequence of PR002299 HC1 | EVQLLESGGGLVQPGGSLRLSCAASGFTFSTYAMNWVRQAPGKGLEWVSRIRSKYNNYATYYADSVKDRFTISRDDSKSTLYLQMNSLRAEDTAVYYCVRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVYTLPPCREEMTKNQVSLWCLVKGFYPSDIAVEWESNGQPENNYKTTPPVLDSDGSFFLYSKLTVDKSRWQQGNVFSCSVMHEALHNHYTQKSLSLSPGK (SEQ ID NO: 4) |
| sequence of PR002299 VH1 | EVQLLESGGGLVQPGGSLRLSCAASGFTFSTYAMNWVRQAPGKGLEWVSRIRSKYNNYATYYADSVKDRFTISRDDSKSTLYLQMNSLRAEDTAVYYCVRHGNFGNSYVSWFAYWGQGTLVTVSS (SEQ ID NO: 62) |
| PR003178/ PR002299 VH1 CDR1 (Combined) | GFTFSTYAMN (SEQ ID NO: 25) |
| PR003178/ PR002299 VH1 CDR2 (Combined) | RIRSKYNNYATYYADSVKD (SEQ ID NO: 38) |
| PR003178/ PR002299 VH1 CDR3 (Combined) | HGNFGNSYVSWFAY (SEQ ID NO: 44) |
| sequence of PR003178/ PR002299LC | QAVVTQEPSLTVSPGGTVTLTCRSSTGAVTTSNYANWVQQKPGQAPRGLIGGTNKRAPWTPARFSGSLLGDKAALTLLGAQPEDEAEYFCALWYSNLWVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS (SEQ ID NO: 47) |
| sequence of PR003178 VL | QAVVTQEPSLTVSPGGTVTLTCRSSTGAVTTSNYANWVQQKPGQAPRGLIGGTNKRAPWTPARFSGSLLGDKAALTLLGAQPEDEAEYFCALWYSNLWVFGGGTKLTVL (SEQ ID NO: 66) |
| PR003178/ PR002299 LCDR1 (Combined) | RSSTGAVTTSNYAN (SEQ ID NO: 50) |
| PR003178/ PR002299 LCDR2 (Combined) | GTNKRAP (SEQ ID NO: 53) |
| PR003178/ PR002299 LCDR3 (Combined) | ALWYSNLWV (SEQ ID NO: 56) |

Example 5. Preparation of BCMA x CD3 Bispecific Antibody

The anti-BCMA antibody and anti-CD3 cells selected from Example 4 were used to prepare bispecific antibody. The prepared bispecific antibody of this BCMAxCD3 bispecific antibody can simultaneously bind two targets, wherein one terminus can recognize BCMA specifically expressed on the surface of a tumor cell, while the other terminus can bind to CD3 molecules on T cells. When the BCMAxCD3 bispecific antibody molecule binds to the surface of a tumor cell, it can recruit and activate the T cells near the tumor cells, thus killing the tumor cells.

Each bispecific antibody involves three protein chains comprising the heavy chain of the corresponding anti-BCMA antibody, as well as the heavy chain and the light chain of the above-mentioned anti-CD3 antibody, respectively. To minimize the formation of by-products containing mismatched heavy chains (e.g. two heavy chains of the anti-CD3 antibody are mismatched), mutated heterodimeric Fc regions carrying "knob-hole" mutations and transformed disulfide bonds were used, as described in WO 2009080251 and WO 2009080252. The BCMA x CD3 bispecific antibody is IgG1 with L234A and L235A mutations in Fc (according to EU index numbering).

Each bispecific antibody was generated by simultaneous co-transfection with three different mammalian expression vectors which encoding: 1) the heavy chain of corresponding BCMA antibody, which carries a "Hole" mutation in Fc region to generate a heterodimeric antibody and carries L234A and L235A mutations in Fc CH3; 2) the heavy chain of corresponding CD3 antibody, which carries a "knob" mutation in Fc region to generate a heterodimeric antibody and carries L234A and L235A mutations in Fc CH3; 3) the light chain of corresponding CD3 antibody, respectively. The "knob" mutation in the Fc region of human IgG1 consists of T366W, and the "Hole" mutation consists of T366S, L368A and Y407V. In addition, the antibody comprises S354C in the Fc region of "knob" and Y349C of "Hole" to form a disulfide bond to increase stability and heterodimeric antibody yield. Tables 5-7 below shows the sequence information of the bispecific antibodies of the present disclosure and positive control 2, respectively.

TABLE 5

| Sequence information of BCMA chain of PR003178 bispecific antibody | |
|---|---|
| Sequence of PR003178 HC2 | EVQLVETGGGLIQPGGSLRLSCAASGFTVSDNYMTWVRQAPGKG<br>LEWVSVIFSGGNTYYADSVKGRFTISRDNAKNTLYLQMNSLRAE<br>DTALYYCARRNYDDTRGTDVFDIWGQGTMVTVSSGGGGSGGGG<br>SGGGGSEVQLVETGGGLIQPGGSLRLSCAASGFTVSDNYMTWVR<br>QAPGKGLEWVSVIFSGGNTYYADSVKGRFTISRDNAKNTLYLQM<br>NSLRAEDTALYYCARRNYDDTRGTDVFDIWGQGTMVTVSSASEP<br>KSSDKTHTCPPCPAPEAAGGPSVFLFPPKPKDTLMISRTPEVTCVV<br>VDVSHEDPEVKFNWYVDGVEVHNAKTKPREEQYNSTYRVVSVL<br>TVLHQDWLNGKEYKCKVSNKALPAPIEKTISKAKGQPREPQVCT<br>LPPSREEMTKNQVSLSCAVKGFYPSDIAVEWESNGQPENNYKTTP<br>PVLDSDGSFFLVSKLTVDKSRWQQGNVFSCSVMHEALHNHYTQK<br>SLSLSPGK (SEQ ID NO: 8) |
| Sequence of PR003178 VH2 | EVQLVETGGGLIQPGGSLRLSCAASGFTVSDNYMTWVRQAPGKG<br>LEWVSVIFSGGNTYYADSVKGRFTISRDNAKNTLYLQMNSLRAE<br>DTALYYCARRNYDDTRGTDVFDIWGQGTMVTVSS (SEQ ID NO: 59) |
| PR003178 VH2 CDR1 (Combined) | GFTVSDNYMT (SEQ ID NO: 22) |
| PR003178 VH2 CDR2 (Combined) | VIFSGGNTYYADSVKG (SEQ ID NO: 33) |
| PR003178 VH2 CDR3 (Combined) | RNYDDTRGTDVFDI (SEQ ID NO: 42) |

TABLE 6

| Amino acid sequence information of BCMA chain of PR002299 bispecific antibody | |
|---|---|
| PR002299 HC2 | EVQLLESGGGLVQPGGSLRLSCAASGFTFSSYAMIWVRQAPGK<br>GLEWVSGISESGGSTYYADSVKGRFTISRDNSKNTLYLQMNSLR<br>AEDTAVYFCVKDLDDILTGYYKDYWGQGTLVTVSSRTGGGGS<br>KLEVQLLESGGGLVQPGGSLRLSCAASGFTFSSYAMIWVRQAPG<br>KGLEWVSGISESGGSTYYADSVKGRFTISRDNSKNTLYLQMNSL<br>RAEDTAVYFCVKDLDDILTGYYKDYWGQGTLVTVSSASEPKSS<br>DKTHTCPPCPAPEAAGGPSVFLFPPKPKDTLMISRTPEVTCVVVD<br>VSHEDPEVKFNWYVDGVEVHNAKTKPREEQYNSTYRVVSVLT<br>VLHQDWLNGKEYKCKVSNKALGAPIEKTISKAKGQPREPQVCT<br>LPPSREEMTKNQVSLSCAVKGFYPSDIAVEWESNGQPENNYKTT<br>PPVLDSDGSFFLVSKLTVDKSRWQQGNVFSCSVMHEALHNHYT<br>QKSLSLSPGK (SEQ ID NO: 7) |
| PR002299 VH2 | EVQLLESGGGLVQPGGSLRLSCAASGFTFSSYAMIWVRQAPGK<br>GLEWVSGISESGGSTYYADSVKGRFTISRDNSKNTLYLQMNSLR<br>AEDTAVYFCVKDLDDILTGYYKDYWGQGTLVTVSS (SEQ ID NO: 60) |
| PR002299 VH2 CDR1 (Combined) | GFTFSSYAMI (SEQ ID NO: 26) |

TABLE 6-continued

| Amino acid sequence information of BCMA chain of PR002299 bispecific antibody | |
|---|---|
| PR002299 VH2 CDR2 (Combined) | GISESGGSTYYADSVKG (SEQ ID NO: 37) |
| PR002299 VH2 CDR3 (Combined) | DLDDILTGYYKDY (SEQ ID NO: 41) |

TABLE 7

Amino acid sequence information of positive control 2 (PR002199)

| PR002199 | Amino acid sequence and sequence number |
|---|---|
| PR002199 HC1 | EVQLVESGGGLVQPGRSLRLSCAASGFTFDDYAMHWVRQ APGKGLEWVSGISWNSGSIGYADSVKGRFTISRDNAKNSLY LQMNSLRAEDTALYYCAKDSRGYGDYRLGGAYWGQGTL VTVSSASTKGPSVFPLAPSSKSTSGGTAALGCLVKDYFPEPV TVSWNSGALTSGVHTFPAVLQSSGLYSLSSVVTVPSSSLGT QTYICNVNHKPSNTKVDKKVEPKSCDKTHTCPPCPAPEAAG GPSVFLFPPKPKDTLMISRTPEVTCVVVDVSHEDPEVKFNW YVDGVEVHNAKTKPREEQYNSTYRVVSVLTVLHQDWLNG KEYKCKVSNKALGAPIEKTISKAKGQPREPQVYTLPPCREE MTKNQVSLWCLVKGFYPSDIAVEWESNGQPENNYKTTPPV LDSDGSFFLYSKLTVDKSRWQQGNVFSCSVMHEALHNHYT QKSLSLSPGK (SEQ ID NO: 3) |
| PR002199 VH1 | EVQLVESGGGLVQPGRSLRLSCAASGFTFDDYAMHWVRQ APGKGLEWVSGISWNSGSIGYADSVKGRFTISRDNAKNSLY LQMNSLRAEDTALYYCAKDSRGYGDYRLGGAYWGQGTL VTVSS (SEQ ID NO: 61) |
| PR002199 VH1 CDR1 (Combined) | GFTFDDYAMH (SEQ ID NO: 23) |
| PR002199 VH1 CDR2 (Combined) | GISWNSGSIGYADSVKG (SEQ ID NO: 35) |
| PR002199 VH1 CDR3 (Combined) | DSRGYGDYRLGGAY (SEQ ID NO: 43) |
| PR002199 HC2 | EVQLLESGGGLVQPGGSLRLSCAASGFTVSSYGMSWVRQA PGKGPEWVSGIRGSDGSTYYADSVKGRFTISRDNSKNTLYL QMNSLRAEDTAVYYCAKQGENDGPFDHRGQGTLVTVSSG GGGSEVQLLESGGGLVQPGGSLRLSCAASGFTVSSYGMSW VRQAPGKGPEWVSGIRGSDGSTYYADSVKGRFTISRDNSKN TLYLQMNSLRAEDTAVYYCAKQGENDGPFDHRGQGTLVT VSSASEPKSSDKTHTCPPCPAPEAAGGPSVFLFPPKPKDTLM ISRTPEVTCVVVDVSHEDPEVKFNWYVDGVEVHNAKTKPR EEQYNSTYRVVSVLTVLHQDWLNGKEYKCKVSNKALGAPI EKTISKAKGQPREPQVCTLPPSREEMTKNQVSLSCAVKGFY PSDIAVEWESNGQPENNYKTTPPVLDSDGSFFLVSKLTVDK SRWQQGNVFSCSVMHEALHNHYTQKSLSLSPGK (SEQ ID NO: 6) |
| PR002199 VH2 | EVQLLESGGGLVQPGGSLRLSCAASGFTVSSYGMSWVRQA PGKGPEWVSGIRGSDGSTYYADSVKGRFTISRDNSKNTLYL QMNSLRAEDTAVYYCAKQGENDGPFDHRGQGTLVTVSS (SEQ ID NO: 57) |
| PR002199 VH2 CDR1 (Combined) | GFTVSSYGMS (SEQ ID NO: 24) |
| PR002199 VH2 CDR2 (Combined) | GIRGSDGSTYYADSVKG (SEQ ID NO: 36) |
| PR002199 VH2 CDR3 (Combined) | QGENDGPFDH ( SEQ ID NO: 39) |

TABLE 7-continued

| Amino acid sequence information of positive control 2 (PR002199) | |
|---|---|
| PR002199 | Amino acid sequence and sequence number |
| PR002199 LC | EIVMTQSPATLSVSPGERATLSCRASQSVSSNLAWYQQKPG QAPRLLIYGASTRATGIPARFSGSGSGTEFTLTISSLQSEDFA VYYCQQYNNWPWTFGQGTKVEIKRTVAAPSVFIFPPSDEQL KSGTASVVCLLNNFYPREAKVQWKVDNALQSGNSQESVTE QDSKDSTYSLSSTLTLSKADYEKHKVYACEVTHQGLSSPVT KSFNRGEC (SEQ ID NO: 46) |
| PR002199 VL | EIVMTQSPATLSVSPGERATLSCRASQSVSSNLAWYQQKPG QAPRLLIYGASTRATGIPARFSGSGSGTEFTLTISSLQSEDFA VYYCQQYNNWPWTFGQGTKVEIK (SEQ ID NO: 65) |
| PR002199 VL CDR1 (Combined) | RASQSVSSNLA (SEQ ID NO: 49) |
| PR002199 VL CDR2 (Combined) | GASTRAT (SEQ ID NO: 52) |
| PR002199 VL CDR3 (Combined) | QQYNNWPWT (SEQ ID NO: 55) |

Example 6. In Vitro Binding Capacity Assay of BCMAxCD3 Bispecific Antibody on NCI-H929 Cell Line with Highly Expressed BCMA with FACS To study the binding activity of the BCMA arm of the BCMAxCD3 bispecific antibody to human BCMA, NCI-H929 cell line with highly expressed BCMA was used for binding experiments with human BCMA at cellular level. Briefly, NCI-H929 cell suspensions were collected. The cell density was adjusted to $1\times10^6$ cells/mL, and the cells were inoculated in 96 well V-bottom plates at 100 μL cells/well (Corning, Cat #: 3894), followed by the addition of test antibodies at 100 μL/well, which is gradient diluted at 3 folds of the concentration with 2 folds of the final concentration. Cells were incubated at 4° C. for 2 hours in the dark. Afterwards, cells were washed twice with 100 μL/well of pre-cooled PBS, centrifuged at 500 g for 5 min at 4° C., and followed by discarding the supernatant. 100 μL/well of fluorescent secondary antibody (Alexa Fluor® 488-conjugated AffiniPure Goat Anti-Human IgG, Fcγ Fragment Specific, Jackson, Cat #:109-545-06, 1:500 dilution) was added and incubated at 4° C. for 1 hour in the dark. Cells were washed twice with 100 μL/well of pre-cooled PBS, centrifuged at 500 g, 4° C. for 5 min, and followed by discarding the supernatant. Finally, the cells were resuspended with 200 μL/well of pre-cooled PBS, and the fluorescence luminescence signal values were read by BD FACS CANTOII.

Figures 3A, 3B:
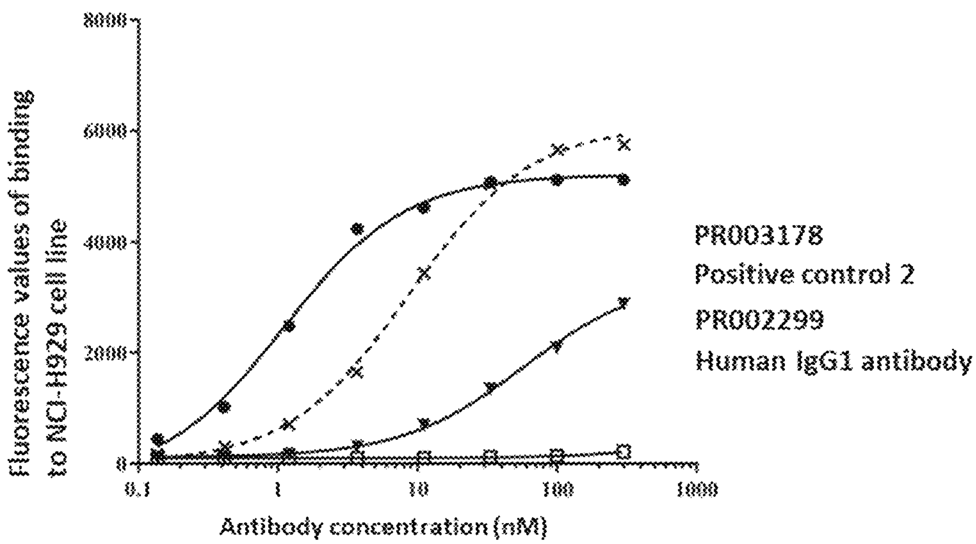
FIGS. 3A and 3B show in vitro binding capacity assay of BCMAxCD3 bispecific antibody on NCI-H929 cell line with highly expressed BCMA with FACS.

As shown in FIGS. 3A and 3B, the binding of BCMAxCD3 bispecific antibody PR003178 to human BCMA molecules on NCI-H929 cell line was superior to that of positive control 2. Specifically, the EC50 of the binding curve of antibody PR003178 was approximately 8 times lower than that of positive control 2. Meanwhile, the binding of antibody PR002299 to human BCMA molecules on NCI-H929 cell line was weaker than that of antibody PR003178 in terms of both the maximum binding fluorescence value and the EC50 of the binding curve.

Example 7. In Vitro Binding Capacity Assay of BCMA x CD3 Bispecific Antibody on HEK293T Cell Strain Overexpressing Human and Cynomolgus Monkey BCMA with FACS To study the in vitro binding activity of the BCMA arm of the BCMAxCD3 bispecific antibody, HEK293T cell strain overexpressing human BCMA (HEK293T/huBCMA) and HEK293T cell strain overexpressing cynomolgus monkey BCMA (HEK293T/cynoBCMA) were used for antibody binding experiments at cellular level. Briefly, HEK293T/huBCMA cells and HEK293T/cynoBCMA cells were digested and resuspended with DMEM complete medium. The cell density of the two was adjusted to $1\times10^6$ cells/mL, respectively. Cells were inoculated at 100 μL cells/well in a 96 well V-bottom plate (Corning, Cat #: 3894), followed by the addition of test antibodies at 100 μL/well, which is gradient diluted at 3 folds of the concentration with 2 folds of the final concentration. Cells were incubated at 4° C. for 1 hour in the dark. Afterwards, the cells were washed twice with 100 μL/well of pre-cooled PBS, centrifuged at 500 g for 5 min at 4° C., and followed by discarding the supernatant. 100 μL/well of fluorescent secondary antibody (Alexa Fluor® 488-conjugated AffiniPure Goat Anti-Human IgG, Fcγ Fragment Specific, Jackson, Cat #: 109-545-06, 1:500 dilution) was added and incubated for 30 min at 4° C. in the dark. Cells were washed twice with 100 μL/well of pre-cooled PBS, centrifuged at 500 g, 4° C. for 5 min, and followed by discarding the supernatant. Finally, the cells were resuspended with 200 μL/well of pre-cooled PBS, and the fluorescence luminescence signal values were read by BD FACS CANTOII.

As shown in FIG. 4A, the binding of BCMAxCD3 bispecific antibody PR003178 to human BCMA on HEK293T/huBCMA cells was stronger than that of positive control 2. Specifically, the EC50 of the binding curve of antibody PR003178 was about 5 times lower than that of positive control 2, as shown in FIG. 4C. Meanwhile, as shown in FIG. 4B, PR003178 was able to cross-bind to cynomolgus monkey BCMA on HEK293T/cynoBCMA cells, while positive control 2 has no ability of cross-binding cynomolgus monkey BCMA.

Example 8. In Vitro Binding Capacity Assay of BCMA x CD3 Bispecific Antibody on Human and Cynomolgus Monkey T Cells with FACS To study the in vitro binding activity of the CD3 arm of the BCMAxCD3 bispecific antibody, human and cynomolgus monkey T cells were used for antibody binding experiments at cellular level. Briefly, the density of human and cynomolgus monkey T cells was adjusted to $1\times10^6$ cells/mL, respectively. Cells were inoculated at 100 μL cells/well in a 96 well V-bottom plate (Corning, Cat #: 3894), followed by the addition of test antibodies at 100 μL/well, which is gradient diluted at 3 folds of the concentration with 2 folds of the final concentration. Cells were incubated at 4° C. for 1 hour in the dark. Afterwards, cells were washed twice with 100 μL/well of pre-cooled PBS, centrifuged at 500 g in 4° C. for 5 min, and followed by discarding the supernatant. 100 μL/fluorescent secondary antibody (Alexa Fluor® 488-conjugated AffiniPure Goat Anti Human IgG, Fcγ Fragment Specific, Jackson, Cat #:109-545-06, 1:500 dilution) was added and incubated for 30 min at 4° C. in the dark. Cells were washed twice with 100 μL/well of pre-cooled PBS, centrifuged at 500 g, 4° C. for 5 min, and followed by discarding the supernatant. Finally, the cells were resuspended with 200 μL/well of pre-cooled PBS, and the fluorescence luminescence signal values were read by BD FACS CANTOII.

Figure 5A:
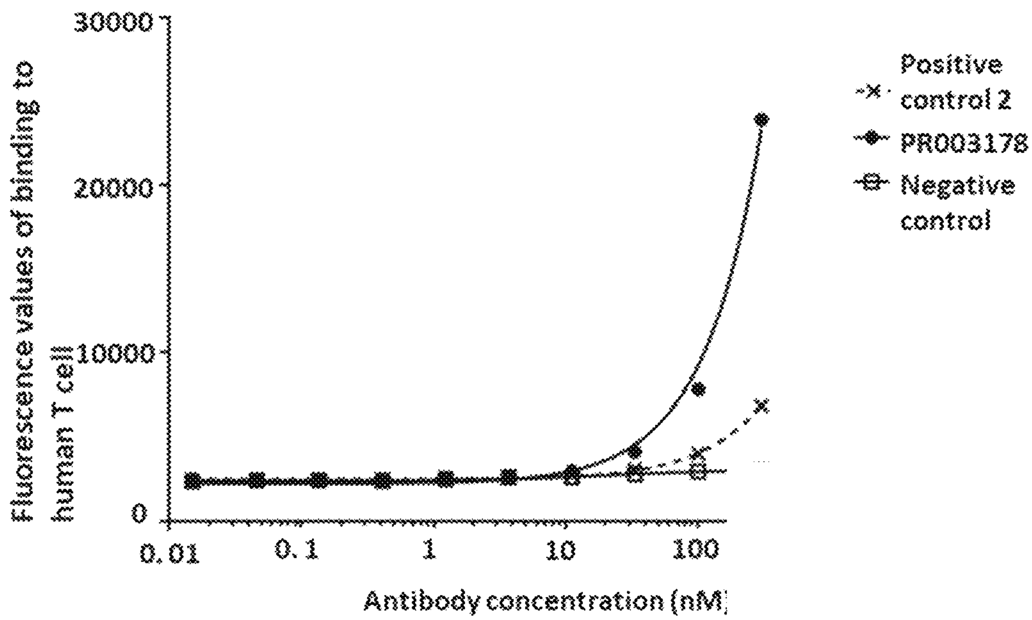
FIGS. 5A and 5B show in vitro binding capacity assay of BCMA x CD3 bispecific antibody on human and cynomolgus monkey T cells with FACS.
Figure 5B:
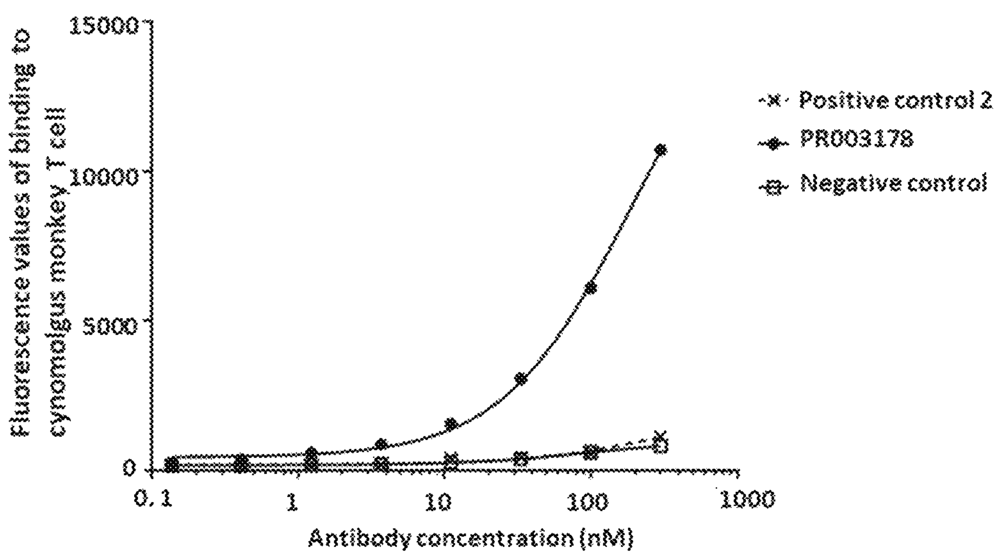
Figure 6A:
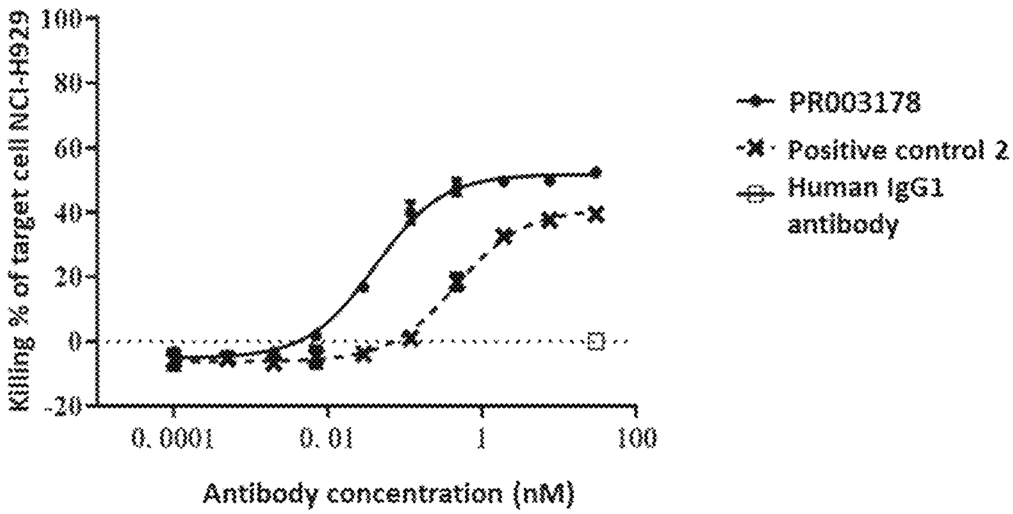
FIGS. 6A-6E show in vitro killing experiment and cytokine release of BCMAxCD3 bispecific antibody against cell line NCI-H929 highly expressing BCMA.
Figure 6B:
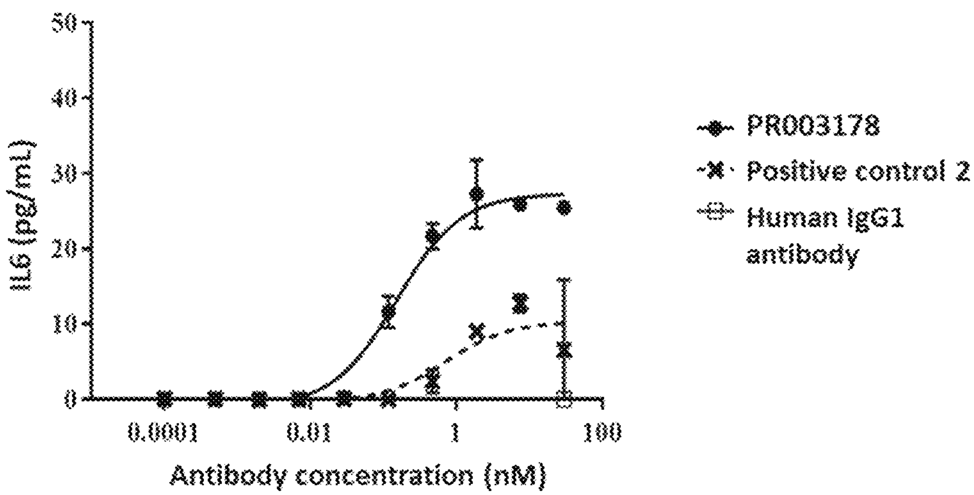
Figures 6C, 6D, 6E:
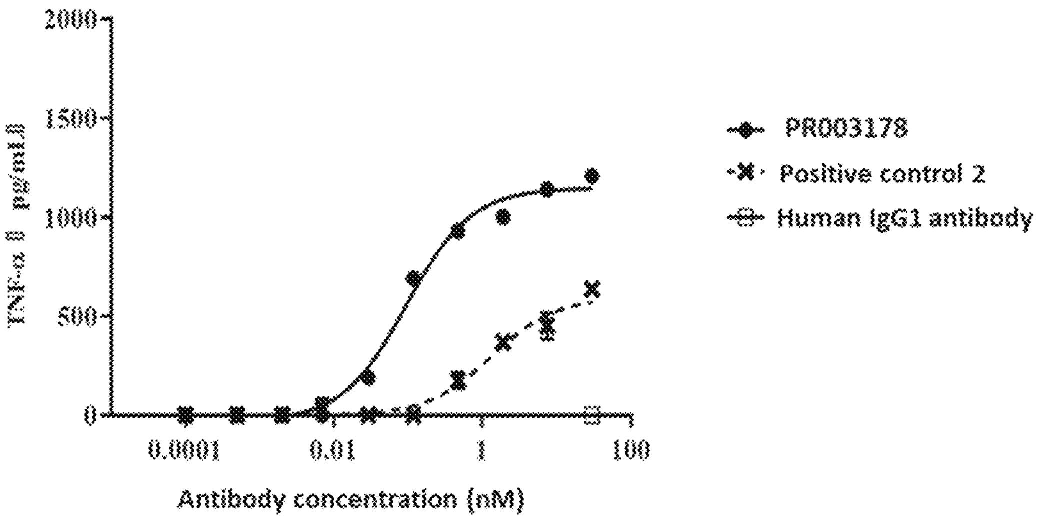
Figure 7A:
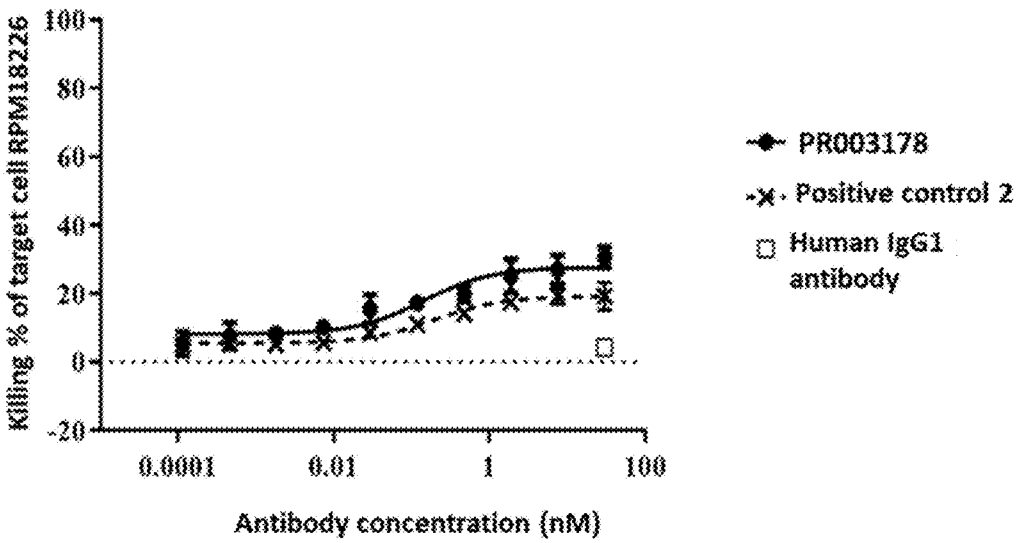
Figure 7B:
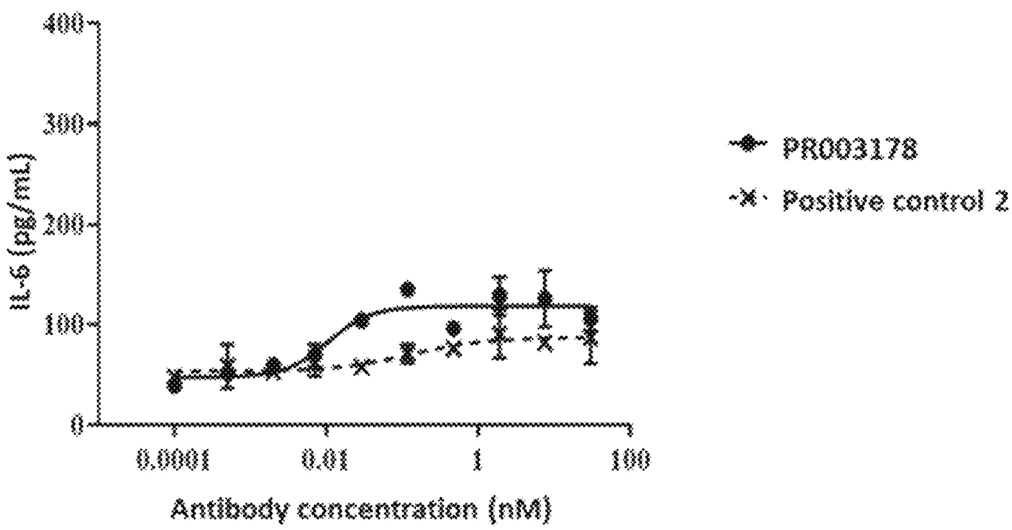
Figure 7C:
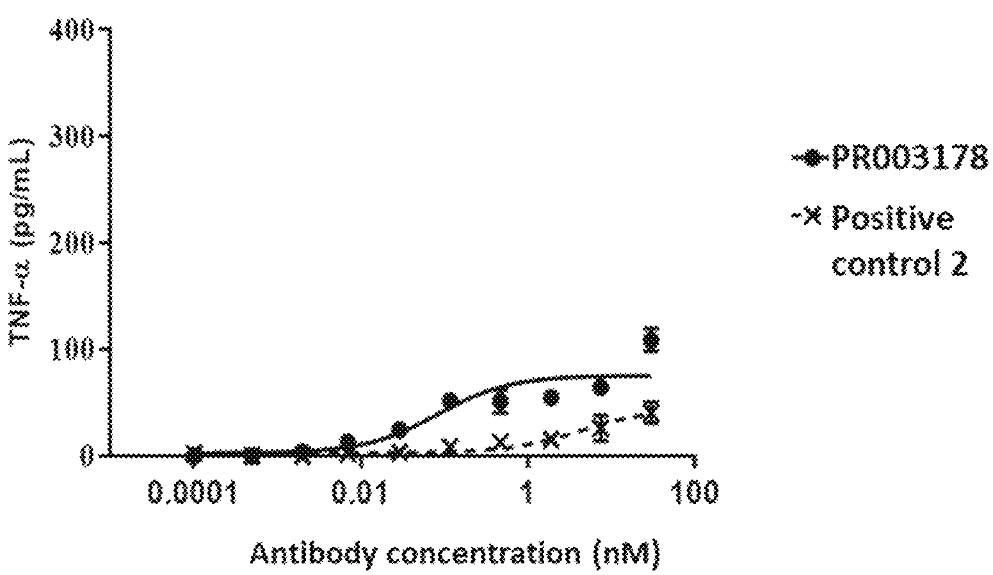

As shown in FIG. 5A, the binding of BCMAxCD3 bispecific antibody PR003178 to human CD3 on human T cells was stronger than that of positive control 2. Specifically, the fluorescence value of PR003178 binding was higher than that of positive control 2 binding at the same antibody concentration. Meanwhile, as shown in FIG. 5B, antibody PR003178 was able to cross-bind to cynomolgus monkey CD3 on cynomolgus monkey T cells, while positive control 2 have no ability of cross-binding cynomolgus monkey BCMA.

Example 9. In Vitro Killing Experiment and Cytokine Release of BCMAxCD3 Bispecific Antibody Against Cell Line NCI-H929 Highly Expressing BCMA To study the in vitro target cell killing ability mediated by BCMAxCD3 bispecific antibody, human PBMC was used as effector cell and NCI-H929 cell line highly expressing BCMA was used as target cell for in vitro killing experiments and cytokine release detection. Specifically, the density of PBMC was adjusted to $1.1\times10^6$ cells/mL and the density of NCI-H929 was adjusted to $0.11\times10^6$ cells/mL by using RPMI1640/5% FBS medium. Each of the two cell suspensions were inocubated at 90 μL cells/well in a 96 well U-bottom plate (Corning, Cat #: 3799), followed by the addition of test antibodies at 20 μL/well, which is gradient diluted at 4 folds of the concentration with 10 folds of the final concentration, wherein the maximum final concentration of antibody is 30 nM, and each antibody has 10 concentrations in total with the final effector-target ratio as 10:1, and two replicates were set. Meanwhile, different controls were set in the plate: ER (0): NCI-H929+PBMC+RPMI1640/5% FBS medium; ESR: PBMC+RPMI1640/5% FBS medium; TSR: NCI-H929+RPMI1640/5% FBS medium; CMB: RPMI1640/5% FBS medium only; TMR: NCI-H929+RPMI1640/5% FBS medium+lysis buffer (added after incubation for 24 hours); VCC: RPMI1640/5% FBS medium+lysis buffer (added after incubation for 24 hours). The 96 well plates were incubated for 24 hours in a C02 incubator at 37° C. After incubation, 50 μl of supernatant was taken into the 96 well plate (Corning, Cat #: 3599), and 50 μl of cytotoxicity test reagent (CytoTox 96® Non-Radioactive Cytotoxicity Test Kit, Promega, USA, cat #G1780) was added and incubated for 30 min at room temperature. The termination solution was added to terminate the reaction, and the OD490 values were read with Enspire (Perkin Elmer). The OD490 values were used to calculate the killing effect according to the following formula, % of specific killing={(ER-CMB)−[(ESR-CMB)+(TSR-CMB)]}/(TMR-VCC) 100%. Cell culture supernatants were collected to detect the release of cytokines IL-6 and TNF-α. ELISA detection method refers to IL-6 (IL-6 Human Uncoated ELISA Kit, Thermo, Cat #: 88-7066-88) and TNF-α (TNF alpha Human Uncoated ELISA Kit, Thermo, Cat #:88-7346-88) kit operating instructions.

As shown in FIGS. 6A-6E, the killing effect of PBMC mediated by BCMAxCD3 bispecific antibody PR003178 against cell line NCI-H929 with highly expressed BCMA was superior to that of positive control 2 (A). Specifically, the killing percentage of PR003178 at high concentration was higher than that of positive control 2, and the EC50 of the killing curve of PR003178 was 10 times less than that of positive control 2 (D). Meanwhile, the release of cytokines IL-6 and TNF-α produced in the killing system of PR003178 was higher than that of positive control 2 (B, C, E).

Example 10. In Vitro Killing Experiment and Cytokine Release of

BCMAxCD3 bispecific antibody against cell line RPMI8226 low expressing BCMA

To study the in vitro target cell killing ability mediated by BCMAxCD3 bispecific antibody, human PBMC were used as effector cell and the cell line RPMI8226 (CAS, CAS Cell Bank) which low expresses BCMA was used as target cell for in vitro killing experiments and cytokine release detection. Specifically, the density of PBMC was adjusted to $1.1\times10^6$ cells/mL and the density of RPMI8226 was adjusted to $0.11\times10^6$ cells/mL by using RPMI1640/5% FBS medium. Each of the two cell suspensions were inoculated at 90 μL cells/well in a 96 well U-bottom plate (Corning, Cat #: 3799), followed by the addition of test antibodies at 20 μL/well, which is gradient diluted at 4 folds of the concentration with 10 folds of the final concentration, wherein the maximum final concentration of antibody was 30 nM, and each antibody has 10 concentrations in total with the final effector-target ratio as 10:1, and two replicates were set. Meanwhile, different controls were set in the plate: ER (0): RPMI8226+PBMC+RPMI1640/5% FBS medium; ESR: PBMC+RPMI1640/5% FBS medium; TSR: RPMI8226+RPMI1640/5% FBS medium; CMB: RPMI1640/5% FBS medium only; TMR: RPMI8226+RPMI1640/5% FBS medium+lysis buffer (added after incubation for 24 hours); VCC: RPMI1640/5% FBS medium+lysis buffer (added after incubation for 24 hours). The 96 well plates were incubated at 37° C. in a $CO_2$ incubator for 24 hours. After incubation, 50 μl of supernatant was added to the 96 well plate (Corning, Cat #: 3599), and 50 μl of cytotoxicity test reagent (CytoTox 96® Non-Radioactive Cytotoxicity Test Kit, Promega, USA, Cat #: G1780) was added and incubated for 30 min at room temperature. The termination solution was added to terminate the reaction, and the OD490 values were read with Enspire (Perkin Elmer). The OD490 values were used to calculate the killing effect according to the following formula, % of specific killing={(ER−CMB)+[(ESR−CMB)+(TSR−CMB)]}/(TMR−VCC) 100%. Cell culture supernatants were collected to detect the release of cytokines IL-6 and TNF-α. ELISA detection method refers to IL-6 (IL-6 Human Uncoated ELISA Kit, Thermo, Cat #: 88-7066-88) and TNF-α (TNF alpha Human Uncoated ELISA Kit, Thermo, Cat #:88-7346-88) kit operating instructions.

As shown in FIGS. 7A-7E, the killing effect of PBMC mediated by BCMAxCD3 bispecific antibody PR003178 against cell line with low BCMA expression was better than that of positive control 2 (A). Specifically, the target cell killing percentage of PR003178 at high concentration was higher than that of positive control 2(D). Meanwhile, the release of cytokines IL-6 and TNF-α produced in the killing system of PR003178 was higher than that of positive control 2 (B, C, E).

Example 11. Binding of BCMAxCD3 Bispecific Antibody to Cell Line HL-60 without BCMA Expression To study the in vitro binding specificity of BCMAxCD3 bispecific antibody, cell line HL-60 (ATCC® CCL-240™) without human BCMA expression was used for antibody binding experiments at cellular level. Briefly, HL-60 cell suspensions were collected. The cell density was adjusted to $1\times10^6$ cells/mL, respectively, and the cells were inoculated at 100 μL cells/well in 96 well V-bottom plates (Corning, Cat #: 3894), followed by the addition of test antibodies at 100 μL/well, which is gradient diluted at 3 folds of the concentration with 2 folds of the final concentration. The maximum final concentration of antibody is 300 nM, and each antibody has 4 concentrations. Cells were incubated at 4° C. for 1 hours in the dark. Afterwards, the cells were washed twice with 100 μL/well of pre-cooled PBS, centrifuged at 500 g in 4° C. for 5 min, and followed by discarding the supernatant. 100 μL/well of fluorescent secondary antibody (Alexa Fluor® 488-conjugated AffiniPure Goat Anti-Human IgG, Fcγ Fragment Specific, Jackson, Cat #:109-545-06, 1:500 dilution) was added and incubated for 30 min at 4° C. in the dark. Cells were washed twice with 100 μL/well of pre-cooled PBS, centrifuged at 500 g for 5 min at 4° C., and followed by discarding the supernatant. Finally, the cells were resuspended with 200 μL/well of pre-cooled PBS, and the fluorescence luminescence signal values were read by BD FACS CANTOII.

Figure 8:
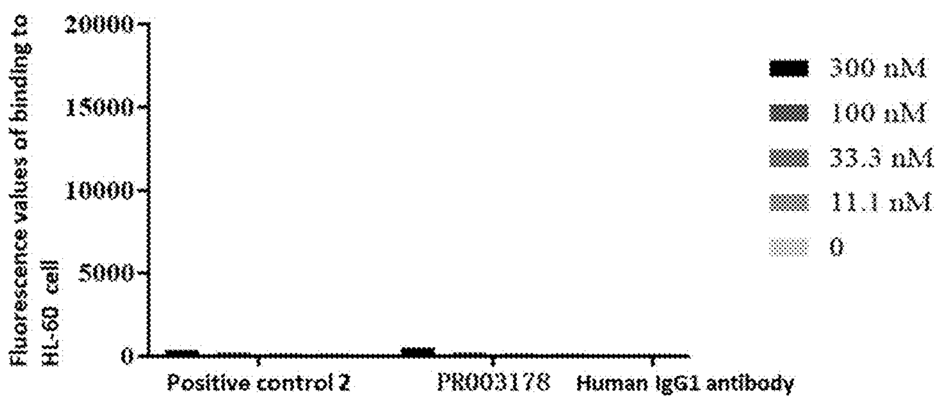
FIG. 8 shows the binding of BCMA x CD3 bispecific antibody to BCMA-negative cell line HL-60 with FACS.

As shown in FIG. 8, BCMAxCD3 bispecific antibody PR003178 and positive control 2 failed to bind non-specifically to the BCMA-negative cell line HL-60 at 300 nM, 100 nM, 33.3 nM and 11.1 nM.

Example 12. Detection of Non-Specific Killing and Cytokine Release of BCMAxCD3 Bispecific Antibody Against BCMA-Negative Cell Line HL60 with FACS To study the specificity of the target cell killing ability mediated by BCMAxCD3 bispecific antibody in vitro, human PBMC was used as effector cell and cell line HL-60 without expressing BCMA was used as target cell for in vitro killing experiments and cytokine release detection. Specifically, target cell HL-60 was labeled with 0.5 μM of CFSE dye. The density of PBMC from three donors was adjusted to $1.1\times10^6$ cells/mL, and the density of CFSE-labeled HL-60 cells was adjusted to $0.11\times10^6$ cells/mL by using RPMI1640/5% FBS medium. Each of the two cell suspensions were inoculated at 90 μL cells/well in a 96 well U-bottom plate (Corning, Cat #: 3799), followed by the addition of test antibodies at 20 μL/well, which has a concentration 10 fold of the final concentration, wherein the final concentrations of antibodies were 100 nM, 30 nM, 10 nM and 3 nM, four concentrations in total. The final effector-target ratio was 10:1. Set two replicates. The 96 well plates were incubated in a $CO_2$ incubator at 37° C. for 24 hours. After incubation, cell culture supernatants were collected to detect the release of cytokines IL-6 and TNF-α. ELISA detection method refers to IL-6 (IL-6 Human Uncoated ELISA Kit, Thermo, Cat #:88- 7066-88) and TNF-α (TNF alpha Human Uncoated ELISA Kit, Thermo, Cat #:88-7346-88) kit operating instructions. The cultured cells were transferred to 96 well V-bottom plates (Corning, Cat #: 3894), stained with 100 μL/well of 7-AAD (BD, Cat #: 559925, 1:100) staining system, and incubated for 30 min at room temperature. The reaction was terminated by adding 100 μL/well of PBS. Detection was performed using BD FACS CANTOII. The killing effect was calculated according to the following formula, % of specific killing=7-AAD+CFSE+ percentage/(7-AAD+CFSE+percentage+7-AAD-CFSE+ percentage)*100%.

Figure 9A:
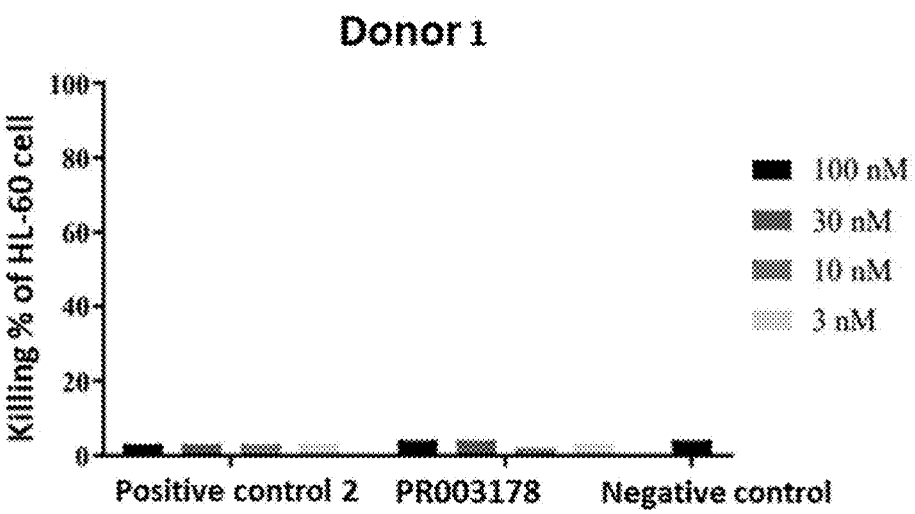
FIGS. 9A-9F show detection of non-specific killing and cytokine release of BCMAxCD3 bispecific antibody against BCMA-negative cell line HL60 with FACS.
Figure 9B:
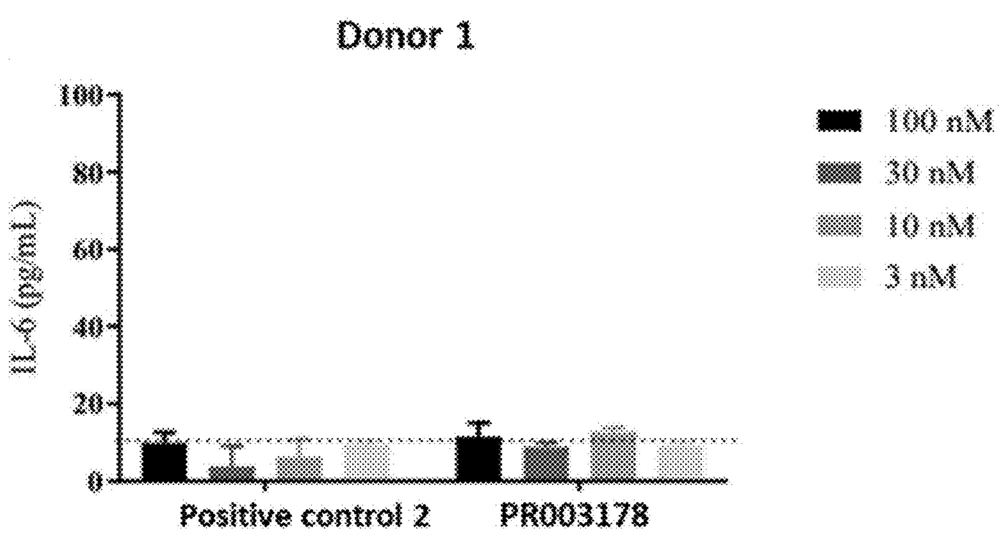
Figure 9C:
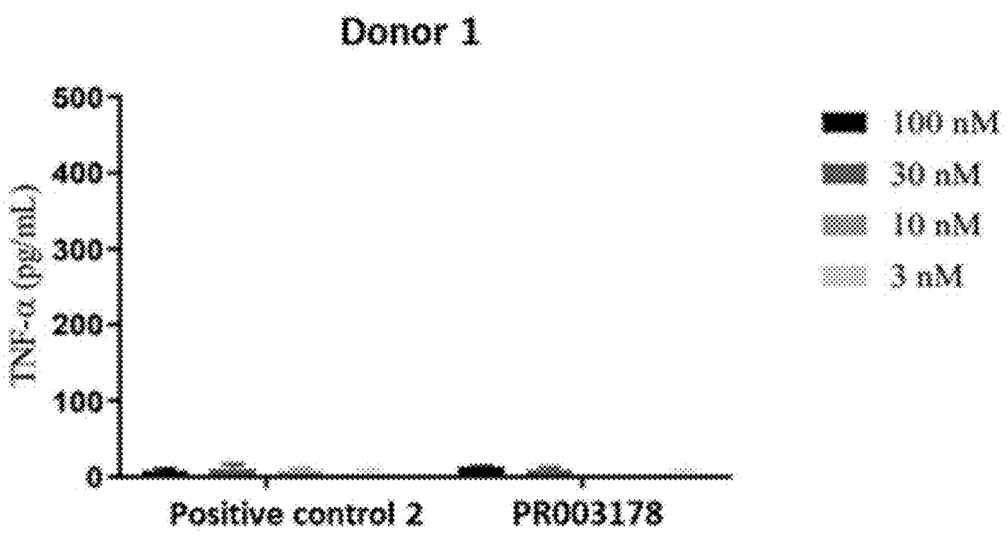
Figure 9D:
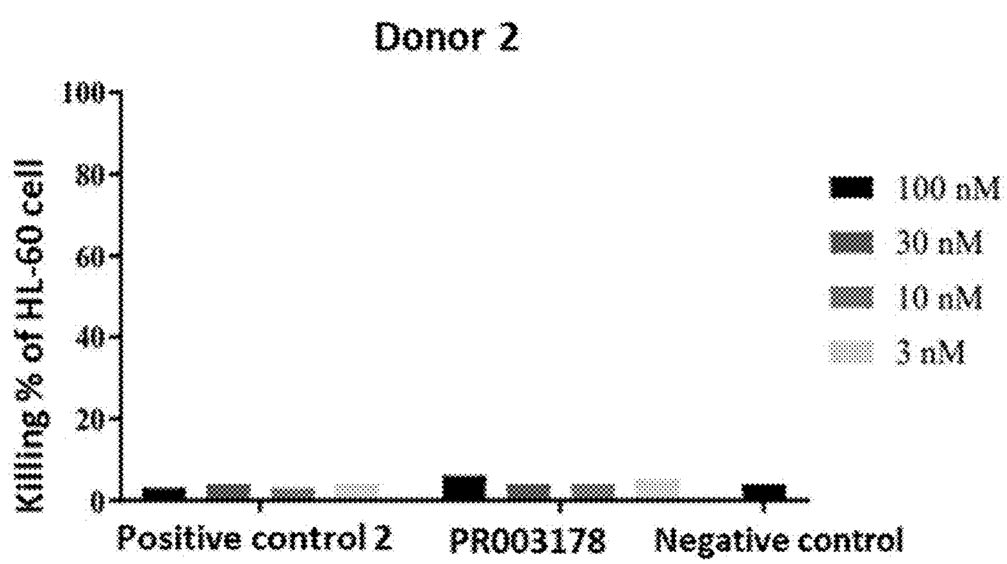
Figure 9E:
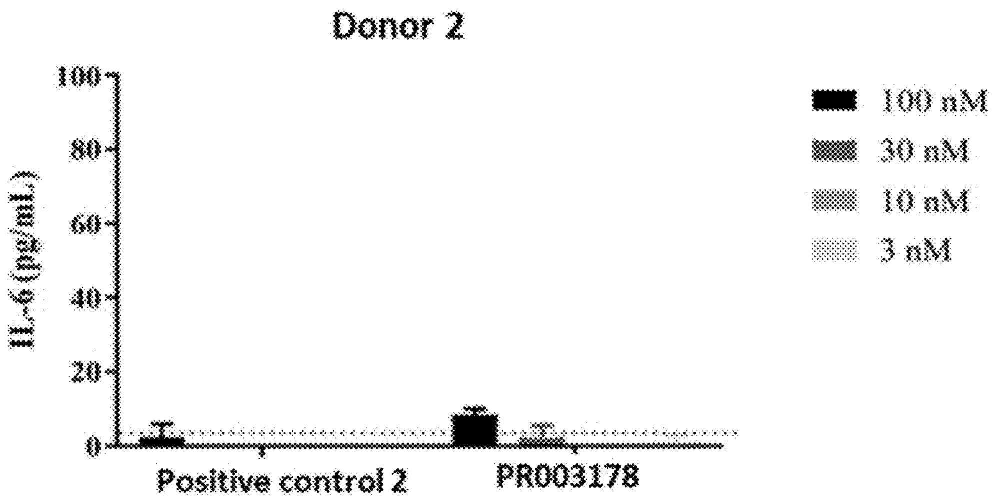
Figure 9F:
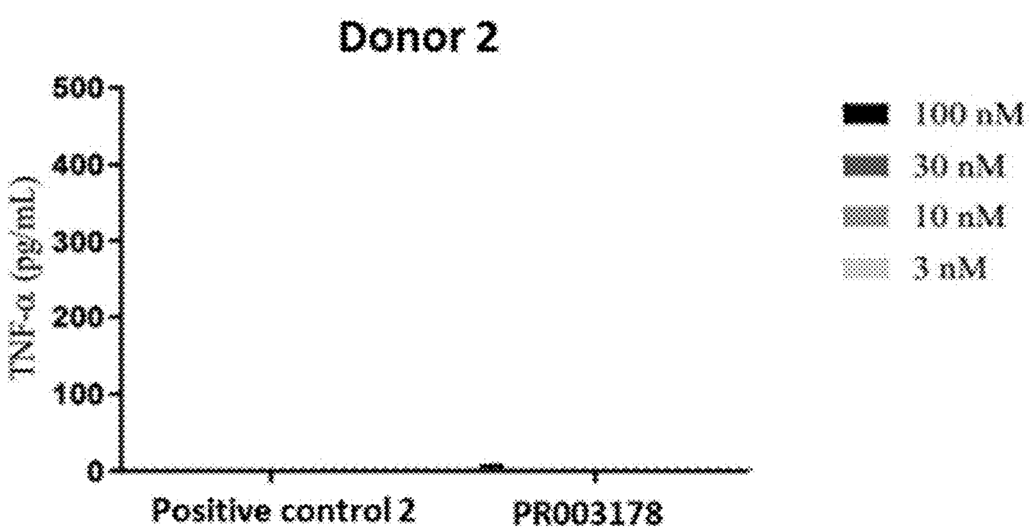

As shown in FIGS. 9A-9E, the BCMAxCD3 bispecific antibody PR003178 and positive control 2 could not mediate the non-specific killing of PBMC from two donors to BCMA negative cell line HL-60 at 100 nM, 30 nM, 10 nM and 3 nM (FIGS. 9A and 9D), and non-specific cytokines IL-6 (FIGS. 9B and 9E) and TNF-α (FIGS. 9C and 9F) could not be detected in this system.

Example 13: Evaluation of Antitumor Efficacy of BCMAxCD3 Bispecific Antibodies in NCI-H929/Human PBMC Mice Model To evaluate the in vivo antitumor efficacy of BCMAxCD3 bispecific antibodies, 6-8 week old female NCG mice were used. All mice were injected intraperitoneally (i.p.) with $3\times10^6$ human PBMC three days before tumor cell inoculation, and then each experimental mouse was inoculated subcutaneously with $5\times10^6$ NCI-H929 cells on the day of tumor cell inoculation. The cells were resuspended in a mixture of PBS and Matrigel (1:1) (0.1 mL per mouse). Mice were randomly grouped into 6 mice in each group when the tumor volume reached 90 $mm^3$. After grouping, the drug diluted with PBS at a specific concentration was administered intravenously (i.v.) once a week in a total of 2 (QW*2), and PBS was used as a mock group. Tumor volume and mice body weight were measured on day 3, 7, 10 and 14 days after the initial administration. Tumor size was calculated by the formula: tumor volume ($mm^3$)=0.5×(tumor length diameter×tumor short diameter$^2$).

Figure 10A:
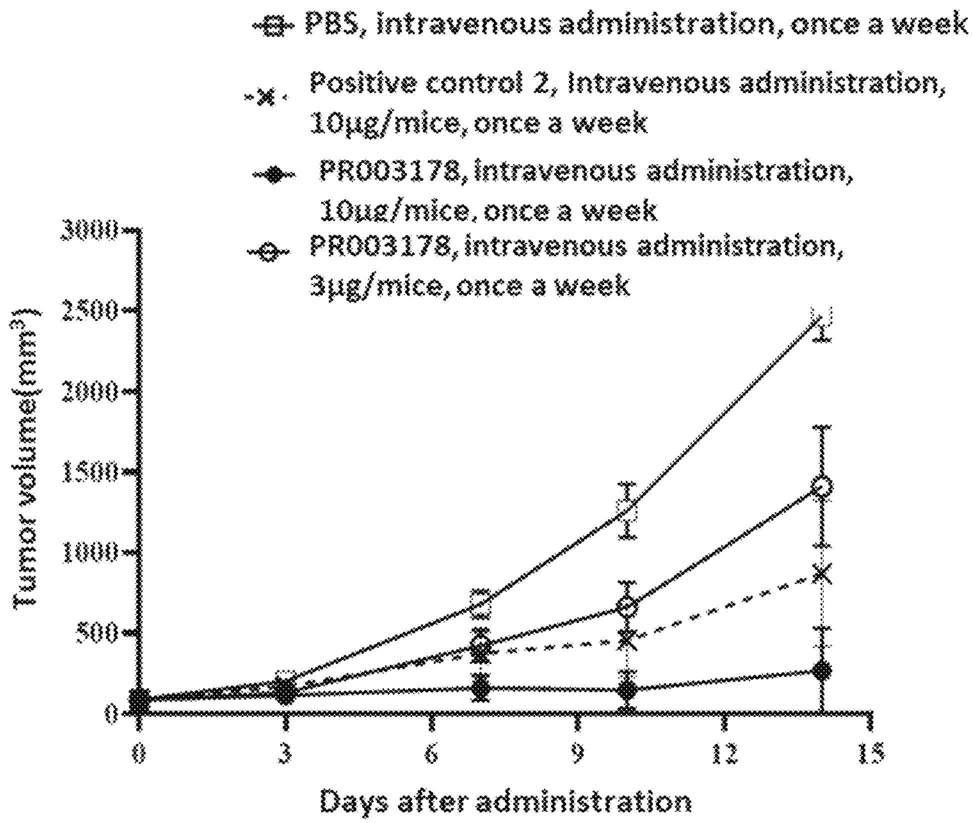
FIGS. 10A and 10B show evaluation of antitumor efficacy of BCMAxCD3 bispecific antibodies in NCI-H929/human PBMC mice model
Figure 10B:
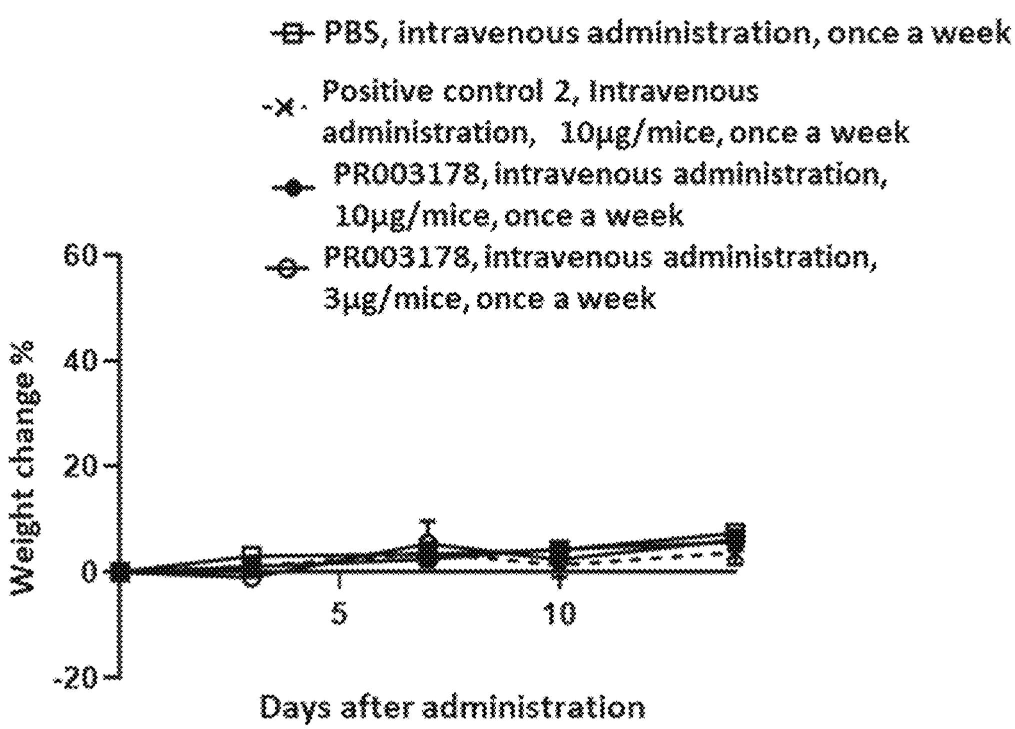

As shown in FIG. 10A, BCMAxCD3 bispecific antibody PR003178 was effective in inhibiting tumor growth at both 10 μg/mouse and 3 μg/mouse, and the efficacy of the 10 μg/mouse group is superior to that of the 3 μg/mouse group. Also, the efficacy of PR003178 at the 10 μg/mouse dose is superior to that of positive control 2 at the same dose. As shown in FIG. 10B, the body weight changes of the mice in each group are within the normal range.

Example 14. Detection for Affinity of PR003178 to Human CD3e/g Recombinant Protein, Cynomolgus Monkey CD3e/g Recombinant Protein, Human BCMA Recombinant Protein and Cynomolgus Monkey BCMA Recombinant Protein with BIACORE HBS-EP+(10 mM HEPES, 150 mM NaCl, 3 mM EDTA and 0.05% P20, pH 7.4, GE Healthcare, Cat #BR-1006-69) was used as running buffer for the entire test, and Series S CM5 (GE Healthcare, Cat #BR-1005-30) was used as the experimental chip. Human BCMA-Fc, Avitag recombinant protein (ACRO, Cat. BC7-H82F0), cynomolgus monkey BCMA-Fc, Avitag (ACRO, Cat. BCA-C82F4) were purchased from ACRO, human CD3e/g ECD-hFc recombinant protein (Lot.20190508002), cynomolgus monkey CD3e/g ECD-hFc recombinant protein and human (Lot.2018040001) were purchased from ChemPartner.

14.1 Coupling of Antigens

The flow rate was set as 10 l/min and four antigens were coupled on four channels on two CM5:1) the injection time was set as 300 s, and 50 mM of NHS and 200 mM of EDC were freshly mixed at 1:1 volume ratio and injected into four channels; 2) human BCMA-Fc, Avitag recombinant protein, cynomolgus monkey BCMA-FC, Avitag, human CD3e/g ECD-hFc recombinant protein and cynomolgus CD3e/g ECD-hFc recombinant protein were all diluted to 1 μg/ml with sodium acetate (Cat #BR-1003-50) (pH 4.5), and injected into channel 2, 3 and 4 of chip 1 and channel 2 of chip 2, respectively; 3) 1 M of ethanolamine (pH8.5) was injected for 300 s to block the remaining active carboxyl groups on the chips surface. After blockage, the instrument was continued to be equilibrated with 1×HBS− EP+ buffer for two hours. The final coupling amounts of human BCMA-Fc, Avitag recombinant protein, cynomolgus monkey BCMA-Fc, Avitag, human CD3e/g ECD-hFc recombinant protein and cynomolgus monkey CD3e/g ECD-hFc recombinant protein were 120 RU, 70 RU, 200 RU and 290 RU, respectively.

14.2 Affinity Determination

A multi-cycle kinetic mode was set, and each cycle included the binding of PR003178 as well as the regeneration of the chip. PR003178 with two-fold gradient dilution was injected into four channels at a flow rate of 30 μl/min. A binding time of 180 s and a dissociation time of 400 s or 600 s were set. Finally, 10 mM of glycine-hydrochloric acid (pH 1.5) (GE Life Sciences, Cat #BR-1003-54) was injected at the same flow rate for 60 s to regenerate the chip.

The experimental results were analyzed by using Biacore T200 analysis software, and channel 1 was deducted as reference channel, and a 1:1 kinetic fit model was selected as the analysis model.

Figure 11A:
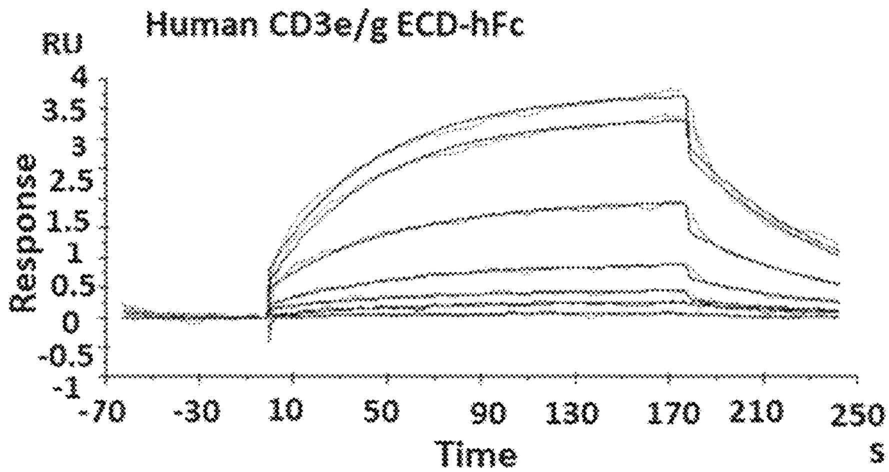
Figure 11B:
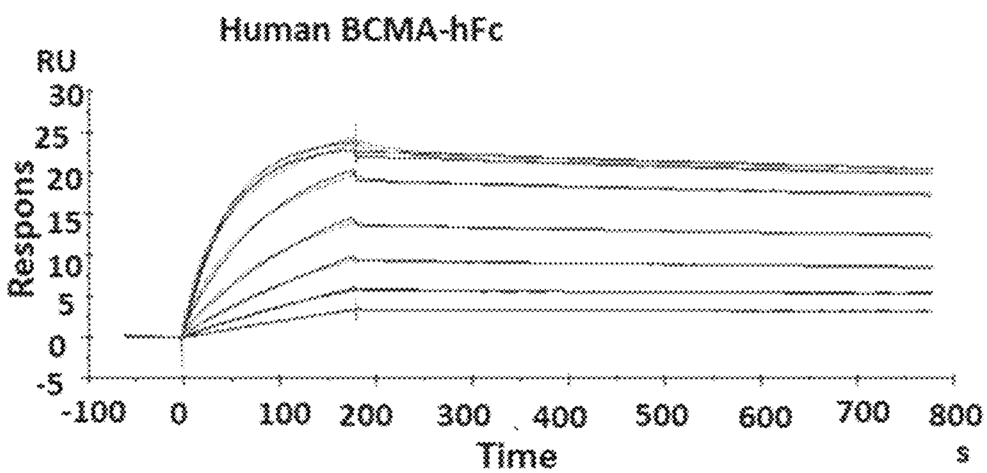

As shown in FIGS. 11B and 11D, BCMAxCD3 bispecific antibody PR003178 binds to human BCMA with high affinity, and the affinity to human BCMA-Fc was about 9.493 E-11 M with excellent cross-binding activity to human and cynomolgus monkey BCMA. As shown in FIGS. 11A and 11C, BCMAxCD3 bispecific antibody PR003178 binds to human CD3 e/g ECD-hFc with the affinity of about 2.541E-08 M and the antibody has excellent cross-binding activity to human and cynomolgus monkey CD3 e/g ECD-hFc. The detailed data including Ka (1/Ms), Kd (1/s) and KD of affinity determination for BCMAxCD3 bispecific antibody PR003178 to BCMA and CD3 e/g ECD-hFc is shown in FIG. 11E.

What is claimed is:

1. A monoclonal antibody or antigen-binding fragments thereof targeting BCMA comprising a heavy chain variable region, wherein the heavy chain variable region comprises HCDR1, HCDR2 and HCDR3 comprising the amino acid sequences of SEQ ID NO: 26, SEQ ID NO: 37 and SEQ ID NO: 41, respectively.

2. The monoclonal antibody or antigen-binding fragments thereof targeting BCMA of claim 1, wherein the heavy chain variable region comprises the amino acid sequence of SEQ ID NO: 60.

3. An isolated nucleic acid encoding the monoclonal antibody or antigen-binding fragments thereof targeting BCMA of claim 1.

4. An isolated expression vector comprising the isolated nucleic acid of claim 3.

5. An isolated host cell comprising the isolated expression vector of claim 4.

6. An antibody drug conjugate comprising the monoclonal antibody or antigen-binding fragments thereof targeting BCMA of claim 1, and a cytotoxic agent.

7. A pharmaceutical composition comprising the monoclonal antibody or antigen-binding fragments thereof targeting BCMA of claim 1, and a pharmaceutically acceptable carrier.

8. A method for treating cancer in a subject in need thereof, comprising: administering an effective amount of the monoclonal antibody or antigen-binding fragments thereof targeting BCMA of claim 1 to the subject.

9. A method for treating cancer in a subject in need thereof, comprising: administering an effective amount of the antibody drug conjugate of claim 6 to the subject.

10. The monoclonal antibody or antigen-binding fragment thereof targeting BCMA of claim 2, wherein the antibody targeting BCMA further comprises an Fc fragment.

11. The monoclonal antibody targeting BCMA of claim 10, wherein the Fc fragment is an Fc fragment of hIgG1, hIgG2, hIgG3 or hIgG4 or a mutant thereof, the mutant of the human heavy chain constant region being selected from the group consisting of: (1) L234A/L235A mutation; (2) knob mutation T366W and hole mutations T366S, L368A and Y407V; (3) knob mutation S354C and hole mutation Y349C.

12. The monoclonal antibody or antigen-binding fragment thereof targeting BCMA of claim 2, the heavy chain of the antibody targeting BCMA has an amino acid sequence of SEQ ID NO: 7.

13. The isolated host cell of claim 5, wherein the isolated host cell is a prokaryotic cell or a eukaryotic cell.

* * * * *